US012558480B2

(12) United States Patent (10) Patent No.: US 12,558,480 B2
Hachey et al. (45) Date of Patent: Feb. 24, 2026

(54) METHODS AND SYSTEMS FOR FILLING IV BAGS WITH THERAPEUTIC FLUID

(71) Applicant: ICU Medical, Inc., San Clemente, CA (US)

(72) Inventors: Jay Hachey, San Clemente, CA (US); Thomas McCall, San Clemente, CA (US); Jason Woodbury, San Clemente, CA (US)

(73) Assignee: ICU Medical, Inc., San Clemente, CA (US)

( * ) Notice: Subject to any disclaimer, the term of this patent is extended or adjusted under 35 U.S.C. 154(b) by 62 days.

(21) Appl. No.: 18/147,231

(22) Filed: Dec. 28, 2022

(65) Prior Publication Data

US 2023/0390490 A1 Dec. 7, 2023

Related U.S. Application Data

(63) Continuation of application No. 15/848,368, filed on Dec. 20, 2017, now Pat. No. 11,541,171, which is a
(Continued)

(51) Int. Cl.
*A61M 5/162* (2006.01)
*A61J 1/20* (2006.01)
(Continued)

(52) U.S. Cl.
CPC ............ *A61M 5/162* (2013.01); *A61J 1/2089* (2013.01); *A61M 5/002* (2013.01); (Continued)

(58) Field of Classification Search
CPC .......... A61M 2005/1402; A61M 39/10; A61M 39/26; A61J 1/10; A61J 1/20; A61J 1/1481; A61J 3/00; Y10S 128/24
See application file for complete search history.

(56) References Cited

U.S. PATENT DOCUMENTS

| 1,923,501 A | 8/1933 | Perry |
| 3,157,201 A | 11/1964 | Littmann |
| | (Continued) | |

FOREIGN PATENT DOCUMENTS

| CN | 1707379 | 12/2005 |
| CN | 101244297 | 8/2008 |
| | (Continued) | |

OTHER PUBLICATIONS

U.S. Appl. No. 29/571,547, filed Jul. 19, 2016, Shauver et al.
(Continued)

*Primary Examiner* — Scott J Medway

(74) *Attorney, Agent, or Firm* — Knobbe, Martens, Olson & Bear, LLP

(57) ABSTRACT

A portable electronic fluid dispensing system can provide pre-filled, pre-primed IV bag assemblies comprising therapeutic fluids. The same fluid line and connector in the IV bag assembly can be used to fill the IV bag as is used to withdraw fluid from the IV bag and infuse such fluid into the patient. The connection points along the IV assembly, such as the connection between the IV bag and a drip chamber, or between an IV bag and tubing, or between a drip chamber and tubing, or between tubing and a closeable, resealable connector, can each be resistant to disconnection by a user. The healthcare practitioner at the patient care site is not required to attach any of these components to each other, and the healthcare practitioner at the patient care site is not required to introduce a spike into a spike port on the IV bag.

15 Claims, 5 Drawing Sheets

Related U.S. Application Data continuation of application No. 14/746,048, filed on Jun. 22, 2015, now Pat. No. 9,849,236, which is a continuation of application No. PCT/US2014/065972, filed on Nov. 17, 2014.

(60) Provisional application No. 61/908,674, filed on Nov. 25, 2013.

(51) Int. Cl.

| | |
|---|---|
| *A61M 5/00* | (2006.01) |
| *A61M 5/14* | (2006.01) |
| *A61M 5/168* | (2006.01) |
| *A61M 39/10* | (2006.01) |
| *A61M 39/22* | (2006.01) |
| *A61J 1/10* | (2006.01) |
| *A61M 5/158* | (2006.01) |

(52) U.S. Cl.

CPC ........ *A61M 5/1411* (2013.01); *A61M 5/1413* (2013.01); *A61M 39/1011* (2013.01); *A61M 39/22* (2013.01); *A61J 1/10* (2013.01); *A61M 2005/1402* (2013.01); *A61M 5/1415* (2013.01); *A61M 2005/1587* (2013.01); *A61M 5/16809* (2013.01)

(56) References Cited

U.S. PATENT DOCUMENTS

| | | | |
|---|---|---|---|
| 3,204,633 | A | 9/1965 | Hofstra et al. |
| 3,344,785 | A | 10/1967 | Hamilton |
| D222,956 | S | 2/1972 | Sato |
| D222,957 | S | 2/1972 | Sato |
| D236,163 | S | 7/1975 | Manno |
| 3,935,883 | A | 2/1976 | Stach et al. |
| 4,005,710 | A | 2/1977 | Zeddies et al. |
| 4,084,606 | A | 4/1978 | Mittleman |
| 4,187,890 | A | 2/1980 | Stach et al. |
| 4,190,048 | A | 2/1980 | Sampson |
| 4,262,671 | A | 4/1981 | Kersten |
| 4,306,705 | A | 12/1981 | Svensson |
| 4,334,535 | A * | 6/1982 | Wilson .................... A61M 5/14 604/82 |
| 4,336,802 | A | 6/1982 | Stone et al. |
| 4,367,736 | A | 1/1983 | Gupton |
| D268,206 | S | 3/1983 | Kosako |
| D268,284 | S | 3/1983 | Manno et al. |
| 4,397,335 | A | 8/1983 | Doblar et al. |
| 4,410,321 | A | 10/1983 | Pearson et al. |
| 4,423,741 | A | 1/1984 | Levy |
| 4,519,792 | A | 5/1985 | Dawe |
| 4,534,758 | A | 8/1985 | Akers et al. |
| 4,559,043 | A | 12/1985 | Whitehouse et al. |
| 4,561,856 | A | 12/1985 | Cochran |
| 4,666,429 | A | 5/1987 | Stone |
| 4,670,007 | A | 6/1987 | Wheeldon et al. |
| 4,683,916 | A | 8/1987 | Raines |
| 4,755,172 | A | 7/1988 | Baldwin |
| 4,759,756 | A | 7/1988 | Forman et al. |
| 4,768,568 | A | 9/1988 | Fournier et al. |
| 4,778,450 | A | 10/1988 | Kamen |
| 4,819,684 | A | 4/1989 | Zaugg et al. |
| 4,863,429 | A | 9/1989 | Baldwin |
| D305,165 | S | 12/1989 | Rudolph et al. |
| 4,922,975 | A | 5/1990 | Polaschegg |
| 4,936,841 | A | 6/1990 | Aoki et al. |
| 4,969,874 | A | 11/1990 | Michel et al. |
| 4,972,876 | A | 11/1990 | Kabata et al. |
| 4,976,590 | A | 12/1990 | Baldwin |
| 4,979,644 | A * | 12/1990 | Meyer .............. A61M 5/16818 222/129 |
| 4,995,268 | A | 2/1991 | Ash et al. |
| 5,024,347 | A | 6/1991 | Baldwin |
| 5,037,390 | A | 8/1991 | Raines et al. |
| 5,114,580 | A | 5/1992 | Ahmad et al. |
| D328,952 | S | 8/1992 | Arioka |
| 5,176,658 | A | 1/1993 | Ranford |
| 5,211,201 | A | 5/1993 | Kamen et al. |
| 5,224,937 | A | 7/1993 | van der Heiden et al. |
| 5,254,096 | A | 10/1993 | Rondelet et al. |
| 5,256,155 | A | 10/1993 | Yerlikaya et al. |
| 5,288,290 | A | 2/1994 | Brody |
| 5,300,044 | A | 4/1994 | Classey et al. |
| D348,101 | S | 6/1994 | Poli et al. |
| 5,334,211 | A | 8/1994 | Shiber |
| 5,336,201 | A | 8/1994 | von der Decken |
| D352,778 | S | 11/1994 | Irvin |
| 5,378,231 | A | 1/1995 | Johnson et al. |
| 5,405,333 | A | 4/1995 | Richmond |
| 5,415,583 | A | 5/1995 | Brandt, Jr. |
| 5,423,791 | A | 6/1995 | Bartlett |
| 5,431,201 | A | 7/1995 | Torchia et al. |
| 5,439,451 | A | 8/1995 | Collinson et al. |
| 5,466,220 | A | 11/1995 | Brenneman |
| 5,609,572 | A | 3/1997 | Lang |
| 5,645,538 | A | 7/1997 | Richmond |
| 5,647,845 | A | 7/1997 | Haber et al. |
| 5,676,346 | A | 10/1997 | Leinsing |
| 5,685,866 | A | 11/1997 | Lopez |
| 5,776,345 | A | 7/1998 | Truitt et al. |
| 5,782,816 | A | 7/1998 | Werschmidt et al. |
| 5,807,312 | A | 9/1998 | Dzwonkiewicz |
| 5,810,792 | A | 9/1998 | Fangrow, Jr. et al. |
| 5,830,185 | A | 11/1998 | Block, Jr. |
| 5,871,110 | A | 2/1999 | Grimard et al. |
| 5,871,500 | A | 2/1999 | Jepson et al. |
| 5,885,270 | A | 3/1999 | Ortiz et al. |
| D408,079 | S | 4/1999 | Ellis |
| 5,897,526 | A | 4/1999 | Vaillancourt |
| 5,904,666 | A | 5/1999 | DeDecker et al. |
| 5,910,252 | A | 6/1999 | Truitt et al. |
| 5,935,106 | A | 8/1999 | Olsen |
| 5,947,951 | A | 9/1999 | Ortiz et al. |
| 5,968,014 | A | 10/1999 | Neftel et al. |
| 5,989,237 | A | 11/1999 | Fowles et al. |
| 6,059,747 | A | 5/2000 | Bruggeman et al. |
| 6,110,153 | A | 8/2000 | Davis et al. |
| RE36,871 | E | 9/2000 | Epstein et al. |
| 6,123,685 | A | 9/2000 | Reynolds |
| 6,132,404 | A | 10/2000 | Lopez |
| 6,152,900 | A | 11/2000 | Mayer |
| 6,171,484 | B1 | 1/2001 | Schnell et al. |
| 6,179,823 | B1 | 1/2001 | Niedospial, Jr. |
| 6,193,675 | B1 | 2/2001 | Kraus et al. |
| 6,193,689 | B1 | 2/2001 | Woodard |
| 6,202,708 | B1 | 3/2001 | Bynum |
| 6,221,041 | B1 | 4/2001 | Russo |
| 6,245,048 | B1 | 6/2001 | Fangrow, Jr. et al. |
| 6,287,289 | B1 | 9/2001 | Niedospial, Jr. |
| 6,302,864 | B1 | 10/2001 | Nowosielski |
| 6,425,497 | B1 | 7/2002 | Chu et al. |
| 6,474,375 | B2 | 11/2002 | Spero et al. |
| 6,485,472 | B1 | 11/2002 | Richmond |
| 6,551,299 | B2 | 4/2003 | Miyoshi et al. |
| 6,558,365 | B2 | 5/2003 | Zinger et al. |
| 6,572,256 | B2 | 6/2003 | Seaton et al. |
| 6,585,229 | B2 | 7/2003 | Cote, Sr. et al. |
| 6,590,167 | B2 | 7/2003 | Clare |
| 6,599,273 | B1 | 7/2003 | Lopez |
| 6,623,455 | B2 | 9/2003 | Small et al. |
| 6,629,956 | B1 | 10/2003 | Polidoro et al. |
| 6,651,956 | B2 | 11/2003 | Miller |
| 6,663,586 | B2 | 12/2003 | Verkaart et al. |
| 6,689,108 | B2 | 2/2004 | Lavi et al. |
| 6,699,230 | B2 | 3/2004 | Jaafar et al. |
| 6,711,460 | B1 | 3/2004 | Reese |
| 6,726,672 | B1 | 4/2004 | Hanly et al. |
| 6,793,651 | B1 | 9/2004 | Bennett et al. |
| 6,813,868 | B2 | 11/2004 | Baldwin et al. |
| 6,854,620 | B2 | 2/2005 | Ramet |
| 6,877,530 | B2 | 4/2005 | Osborne et al. |
| 6,908,459 | B2 | 6/2005 | Harding et al. |
| 6,915,823 | B2 | 7/2005 | Osborne et al. |

(56)　　　　　　References Cited

U.S. PATENT DOCUMENTS

| | | | |
|---|---|---|---|
| 6,948,522 B2 | 9/2005 | Newbrough et al. |
| 6,953,450 B2 | 10/2005 | Baldwin et al. |
| 6,985,870 B2 | 1/2006 | Martucci et al. |
| 6,991,002 B2 | 1/2006 | Osborne et al. |
| 6,994,315 B2 | 2/2006 | Ryan et al. |
| 6,997,917 B2 | 2/2006 | Niedospial, Jr. et al. |
| 7,006,894 B2 | 2/2006 | De La Huerga |
| 7,017,623 B2 | 3/2006 | Tribble et al. |
| 7,086,431 B2 | 8/2006 | D'Antonio et al. |
| 7,108,024 B2 | 9/2006 | Navarro |
| 7,117,901 B2 | 10/2006 | Martinell Gisper-Sauch et al. |
| 7,117,902 B2 | 10/2006 | Osborne |
| 7,128,105 B2 | 10/2006 | Tribble et al. |
| 7,163,031 B2 | 1/2007 | Graves et al. |
| 7,163,035 B2 | 1/2007 | Khan et al. |
| 7,175,615 B2 | 2/2007 | Hanly et al. |
| 7,194,336 B2 | 3/2007 | DiGianfilippo et al. |
| 7,260,447 B2 | 8/2007 | Osborne |
| 7,317,967 B2 | 1/2008 | DiGianfilippo et al. |
| 7,343,224 B2 | 3/2008 | DiGianfilippo et al. |
| 7,343,943 B2 | 3/2008 | Khan et al. |
| 7,351,226 B1 | 4/2008 | Herskowitz |
| 7,354,426 B2 | 4/2008 | Young |
| 7,392,638 B2 | 7/2008 | Baldwin et al. |
| 7,396,051 B2 | 7/2008 | Baldwin et al. |
| 7,398,802 B2 | 7/2008 | Baker |
| 7,418,981 B2 | 9/2008 | Baker et al. |
| 7,442,186 B2 | 10/2008 | Blomquist |
| 7,488,311 B2 | 2/2009 | Domkowski et al. |
| 7,499,581 B2 | 3/2009 | Tribble et al. |
| 7,527,619 B2 | 5/2009 | Domkowski et al. |
| 7,530,211 B2 | 5/2009 | McErlean et al. |
| 7,530,974 B2 | 5/2009 | Domkowski et al. |
| 7,538,858 B2 | 5/2009 | Mackey |
| D594,120 S | 6/2009 | Berberich et al. |
| D596,291 S | 7/2009 | Berberich et al. |
| 7,566,326 B2 | 7/2009 | Duchon et al. |
| 7,610,115 B2 | 10/2009 | Rob et al. |
| 7,630,788 B1 | 12/2009 | Reese |
| 7,630,789 B2 | 12/2009 | Broadfield et al. |
| 7,632,261 B2 | 12/2009 | Zinger et al. |
| 7,654,976 B2 | 2/2010 | Peterson et al. |
| 7,681,606 B2 | 3/2010 | Khan et al. |
| 7,685,026 B1 | 3/2010 | McGrady et al. |
| D616,092 S | 5/2010 | Domkowski et al. |
| 7,717,897 B2 | 5/2010 | Burg et al. |
| D620,108 S | 7/2010 | Eitenmueller et al. |
| 7,753,085 B2 | 7/2010 | Tribble et al. |
| 7,758,560 B2 | 7/2010 | Connell et al. |
| 7,789,850 B2 | 9/2010 | Roger |
| 7,814,731 B2 | 10/2010 | Bender et al. |
| 7,850,051 B2 | 12/2010 | Py et al. |
| 7,867,215 B2 | 1/2011 | Akerlund et al. |
| 7,882,863 B2 | 2/2011 | Pestotnik et al. |
| 7,900,658 B2 | 3/2011 | Osborne et al. |
| 7,913,720 B2 | 3/2011 | Tribble et al. |
| 7,963,201 B2 | 6/2011 | Willoughby et al. |
| 7,963,954 B2 | 6/2011 | Kavazov |
| 7,967,202 B2 | 6/2011 | Durrell et al. |
| 7,981,381 B2 | 7/2011 | Lurvey et al. |
| 7,997,304 B2 | 8/2011 | Ranalletta et al. |
| 8,034,041 B2 | 10/2011 | Domkowski et al. |
| 8,037,659 B2 | 10/2011 | Osborne et al. |
| 8,075,545 B2 | 12/2011 | Moy et al. |
| 8,091,727 B2 | 1/2012 | Domkowski |
| 8,091,860 B2 | 1/2012 | Thompson et al. |
| 8,104,644 B2 | 1/2012 | Py et al. |
| 8,117,809 B2 | 2/2012 | McErlean et al. |
| 8,140,351 B2 | 3/2012 | Tribble et al. |
| 8,141,601 B2 | 3/2012 | Fehr et al. |
| 8,151,835 B2 | 4/2012 | Khan et al. |
| 8,162,903 B2 | 4/2012 | Reilly et al. |
| 8,162,914 B2 | 4/2012 | Kraushaar et al. |
| 8,162,915 B2 | 4/2012 | Brandenburger et al. |
| D660,423 S | 5/2012 | Hermle |

| | | | |
|---|---|---|---|
| 8,172,823 B2 | 5/2012 | Rondeau et al. |
| 8,182,744 B2 | 5/2012 | Mlodzinski et al. |
| 8,197,459 B2 | 6/2012 | Jansen et al. |
| 8,206,367 B2 | 6/2012 | Warren et al. |
| D664,647 S | 7/2012 | Becker |
| D664,648 S | 7/2012 | Becker |
| D664,649 S | 7/2012 | Becker |
| 8,209,941 B2 | 7/2012 | Osborne et al. |
| 8,216,207 B2 | 7/2012 | Moy et al. |
| 8,220,503 B2 | 7/2012 | Tribble et al. |
| 8,220,504 B2 | 7/2012 | Hartman et al. |
| 8,221,382 B2 | 7/2012 | Moy et al. |
| 8,225,824 B2 | 7/2012 | Eliuk et al. |
| 8,225,826 B2 | 7/2012 | Horppu et al. |
| 8,231,567 B2 | 7/2012 | Tennican et al. |
| 8,231,749 B2 | 7/2012 | Dent et al. |
| 8,241,265 B2 | 8/2012 | Moy et al. |
| D667,946 S | 9/2012 | Levesque et al. |
| 8,267,129 B2 | 9/2012 | Doherty et al. |
| 8,267,912 B2 | 9/2012 | Ferris |
| 8,287,513 B2 | 10/2012 | Ellstrom et al. |
| 8,328,082 B1 | 12/2012 | Bochenko et al. |
| 8,336,587 B2 | 12/2012 | Rosenquist et al. |
| 8,353,318 B2 | 1/2013 | Ranalletta et al. |
| 8,356,644 B2 | 1/2013 | Chong et al. |
| 8,356,645 B2 | 1/2013 | Chong et al. |
| 8,357,137 B2 | 1/2013 | Yandell |
| 8,374,887 B1 | 2/2013 | Alexander |
| 8,381,776 B2 | 2/2013 | Horppu |
| 8,382,696 B2 | 2/2013 | Beiriger et al. |
| 8,386,070 B2 | 2/2013 | Eliuk et al. |
| 8,403,905 B2 | 3/2013 | Yow |
| 8,409,165 B2 | 4/2013 | Niedospial, Jr. et al. |
| 8,414,556 B2 | 4/2013 | Garfield et al. |
| 8,425,487 B2 | 4/2013 | Beiriger et al. |
| 8,430,859 B2 | 4/2013 | McConnell |
| 8,449,521 B2 | 5/2013 | Thorne, Jr. et al. |
| D687,948 S | 8/2013 | Levesque et al. |
| 8,506,548 B2 | 8/2013 | Okiyama |
| 8,522,832 B2 | 9/2013 | Lopez et al. |
| 8,551,037 B2 | 10/2013 | Suchecki et al. |
| 8,562,583 B2 | 10/2013 | Akerlund et al. |
| 8,562,584 B2 | 10/2013 | Beiriger et al. |
| 8,567,235 B2 | 10/2013 | Bojan et al. |
| 8,571,708 B2 | 10/2013 | Rob et al. |
| 8,602,067 B2 | 12/2013 | Kuhni et al. |
| 8,608,723 B2 | 12/2013 | Lev et al. |
| 8,622,985 B2 | 1/2014 | Ellstrom |
| 8,636,720 B2 | 1/2014 | Truitt et al. |
| 8,639,525 B2 | 1/2014 | Levine et al. |
| 8,679,075 B2 | 3/2014 | Lurvey et al. |
| 8,684,994 B2 | 4/2014 | Lev et al. |
| 8,701,696 B2 | 4/2014 | Guala |
| 8,702,675 B2 | 4/2014 | Imai |
| 8,720,496 B2 | 5/2014 | Huwiler et al. |
| 8,721,612 B2 | 5/2014 | Domkowski et al. |
| 8,721,614 B2 | 5/2014 | Takemoto et al. |
| 8,721,627 B2 | 5/2014 | Alpert |
| D706,415 S | 6/2014 | Levesque et al. |
| 8,753,325 B2 | 6/2014 | Lev et al. |
| 8,763,798 B2 | 7/2014 | Paul |
| 8,795,231 B2 | 8/2014 | Chong et al. |
| 8,801,689 B2 | 8/2014 | Moy et al. |
| 8,821,436 B2 | 9/2014 | Mosler et al. |
| 8,834,444 B2 | 9/2014 | Domkowski |
| 8,852,147 B2 | 10/2014 | Callan et al. |
| 8,863,788 B2 | 10/2014 | Ranalletta et al. |
| 8,864,725 B2 | 10/2014 | Ranalletta et al. |
| 8,864,737 B2 | 10/2014 | Hasegawa et al. |
| 8,870,832 B2 | 10/2014 | Raday et al. |
| 8,882,718 B2 * | 11/2014 | Mullet .................. A61M 25/02 |
| | | 604/164.08 |
| 8,882,739 B2 | 11/2014 | Domkowski et al. |
| 8,894,627 B2 | 11/2014 | Garfield et al. |
| 8,911,421 B2 | 12/2014 | Domkowski et al. |
| D721,803 S | 1/2015 | Dubach |
| 8,926,554 B2 | 1/2015 | Okuda et al. |
| 8,958,112 B2 | 2/2015 | Matsui et al. |
| D724,198 S | 3/2015 | Oostman et al. |

(56) References Cited

U.S. PATENT DOCUMENTS

| | | | |
|---|---|---|---|
| 8,973,622 B2 | 3/2015 | Lopez et al. | |
| 8,979,792 B2 | 3/2015 | Lev et al. | |
| 9,033,006 B2 | 5/2015 | Perazzo et al. | |
| 9,043,019 B2 | 5/2015 | Eliuk et al. | |
| 9,056,164 B2 | 6/2015 | Tate et al. | |
| 9,057,363 B2 | 6/2015 | Capone | |
| 9,057,370 B2 | 6/2015 | Mundt et al. | |
| 9,060,923 B2 | 6/2015 | Hossainy | |
| 9,061,130 B2 | 6/2015 | Truitt et al. | |
| 9,076,115 B2 | 7/2015 | Utech et al. | |
| 9,079,686 B2 | 7/2015 | Domkowski et al. | |
| 9,089,474 B2 | 7/2015 | Cederschiöld | |
| 9,089,647 B2 | 7/2015 | Haenggi et al. | |
| 9,101,717 B2 | 8/2015 | Mansour et al. | |
| 9,114,242 B2 | 8/2015 | Fangrow, Jr. et al. | |
| 9,132,062 B2 | 9/2015 | Fangrow | |
| 9,132,063 B2 | 9/2015 | Lev et al. | |
| 9,139,316 B2 | 9/2015 | Husnu et al. | |
| 9,144,646 B2 | 9/2015 | Barron, III et al. | |
| 9,149,576 B2 | 10/2015 | Bullington et al. | |
| 9,198,832 B2 | 12/2015 | Moy et al. | |
| 9,211,231 B2 | 12/2015 | Mansour et al. | |
| 9,212,762 B2 | 12/2015 | Duncan | |
| 9,220,661 B2 | 12/2015 | Garfield et al. | |
| D747,472 S | 1/2016 | Bradley et al. | |
| 9,227,048 B2 | 1/2016 | Frattini | |
| 9,241,875 B2 | 1/2016 | Davis et al. | |
| 9,242,039 B2 | 1/2016 | Valk et al. | |
| 9,270,890 B2 | 2/2016 | Okuma et al. | |
| 9,345,640 B2 | 5/2016 | Mosler | |
| 9,345,641 B2 | 5/2016 | Kraus et al. | |
| 9,345,643 B2 | 5/2016 | Okiyama | |
| 9,381,135 B2 | 7/2016 | Reynolds et al. | |
| 9,381,137 B2 | 7/2016 | Garfield et al. | |
| 9,382,021 B2 | 7/2016 | Tribble et al. | |
| 9,402,786 B2 | 8/2016 | Petrone | |
| 9,408,966 B2 | 8/2016 | Kamen | |
| 9,466,088 B2 | 10/2016 | Perazzo et al. | |
| 9,474,690 B2 | 10/2016 | Ranalletta et al. | |
| 9,475,019 B2 | 10/2016 | Kaucky et al. | |
| 9,481,477 B2 | 11/2016 | Kjar | |
| D774,192 S | 12/2016 | Fuchs | |
| D775,325 S | 12/2016 | Larson et al. | |
| 9,511,989 B2 | 12/2016 | Lopez et al. | |
| 9,561,893 B2 | 2/2017 | Root et al. | |
| 9,579,255 B2 | 2/2017 | Eliuk et al. | |
| 9,615,997 B2 | 4/2017 | Fangrow | |
| 9,744,102 B2 | 8/2017 | Kubo | |
| 9,770,388 B2 | 9/2017 | Noike et al. | |
| 9,775,778 B2 | 10/2017 | Qiu et al. | |
| 9,801,787 B2 | 10/2017 | Py | |
| 9,802,171 B2 | 10/2017 | Konrad, Jr. et al. | |
| 9,802,172 B2 | 10/2017 | Konrad, Jr. et al. | |
| D803,396 S | 11/2017 | Oberkircher et al. | |
| 9,827,163 B2 | 11/2017 | Lopez et al. | |
| 9,827,680 B2 | 11/2017 | Davey et al. | |
| D804,651 S | 12/2017 | Loonan | |
| 9,833,605 B2 | 12/2017 | Sanders et al. | |
| 9,849,236 B2 | 12/2017 | Hachey et al. | |
| 9,883,987 B2 | 2/2018 | Lopez et al. | |
| 9,930,297 B2 | 3/2018 | Alexander et al. | |
| 9,931,276 B2 | 4/2018 | Lopez et al. | |
| D819,414 S | 6/2018 | Solomon | |
| 10,106,278 B2 | 10/2018 | Chang et al. | |
| 10,143,985 B2 | 12/2018 | Brown et al. | |
| D837,983 S | 1/2019 | Fangrow | |
| 10,181,186 B2 | 1/2019 | Kriheli et al. | |
| 10,188,849 B2 | 1/2019 | Fangrow | |
| 10,189,616 B2 | 1/2019 | Kraft | |
| D846,146 S | 4/2019 | Amos et al. | |
| 10,259,608 B2 | 4/2019 | Fianchini et al. | |
| D851,745 S | 6/2019 | Shauver et al. | |
| 10,307,338 B2 | 6/2019 | Hellenbrand | |
| 10,314,764 B2 | 6/2019 | Lopez et al. | |
| 10,314,765 B2 | 6/2019 | Lopez et al. | |
| 10,315,174 B2 | 6/2019 | Konrad, Jr. et al. | |
| 10,327,987 B1 | 6/2019 | Bochenko et al. | |
| 10,327,988 B2 | 6/2019 | Tribble et al. | |
| 10,336,477 B2 | 7/2019 | Perazzo et al. | |
| 10,417,758 B1 | 9/2019 | Alexander | |
| 10,420,927 B2 | 9/2019 | Fangrow | |
| 10,494,126 B2 | 12/2019 | Joplin | |
| 10,503,873 B2 | 12/2019 | Prince et al. | |
| 10,512,885 B2 | 12/2019 | Janders et al. | |
| D874,644 S | 2/2020 | Shauver et al. | |
| 10,554,937 B2 | 2/2020 | Alexander et al. | |
| 10,556,062 B2 | 2/2020 | Simpson et al. | |
| 10,576,211 B2 | 3/2020 | Hang et al. | |
| D887,577 S | 6/2020 | Shor et al. | |
| 10,791,975 B2 | 10/2020 | Wilkinson et al. | |
| D905,228 S | 12/2020 | Shauver et al. | |
| 11,007,119 B2 | 5/2021 | Lopez et al. | |
| 11,020,541 B2 | 6/2021 | Fangrow et al. | |
| 11,033,459 B2 | 6/2021 | Ariagno et al. | |
| 11,135,416 B2 | 10/2021 | Fangrow | |
| D943,732 S | 2/2022 | Shauver et al. | |
| D948,044 S | 4/2022 | Fangrow | |
| 11,439,570 B2 | 9/2022 | Lopez et al. | |
| 11,439,571 B2 | 9/2022 | Lopez et al. | |
| 11,541,171 B2 | 1/2023 | Hachey et al. | |
| 11,583,637 B2 | 2/2023 | Fangrow et al. | |
| 11,590,057 B2 | 2/2023 | Tagliamento et al. | |
| 11,806,308 B2 | 11/2023 | Lopez et al. | |
| 11,865,295 B2 | 1/2024 | Fangrow | |
| D1,018,849 S | 3/2024 | Fangrow | |
| 11,951,293 B2 | 4/2024 | Fangrow et al. | |
| 12,023,304 B2 | 7/2024 | Lopez et al. | |
| 12,186,270 B2 | 1/2025 | Lopez et al. | |
| 12,280,249 B2 | 4/2025 | Fangrow et al. | |
| 2002/0017328 A1 | 2/2002 | Loo | |
| 2002/0064880 A1 | 5/2002 | Merten et al. | |
| 2002/0085952 A1 | 7/2002 | Ellingboe et al. | |
| 2002/0095121 A1 | 7/2002 | Norton et al. | |
| 2002/0179544 A1 | 12/2002 | Johnson et al. | |
| 2002/0189712 A1 | 12/2002 | Safabash | |
| 2003/0023226 A1 | 1/2003 | Lopez | |
| 2003/0153895 A1 | 8/2003 | Leinsing | |
| 2003/0188897 A1 | 10/2003 | Ludi et al. | |
| 2003/0236500 A1 | 12/2003 | Scheu | |
| 2004/0031756 A1 | 2/2004 | Suzuki et al. | |
| 2004/0035743 A1 | 2/2004 | Tighe et al. | |
| 2004/0073161 A1 | 4/2004 | Tachibana | |
| 2004/0087888 A1 | 5/2004 | Digianfilippo et al. | |
| 2004/0116891 A1 | 6/2004 | Curutcharry | |
| 2004/0118477 A1 | 6/2004 | Desmond | |
| 2004/0138627 A1 | 7/2004 | Forrest | |
| 2004/0162515 A1 | 8/2004 | Chornenky et al. | |
| 2004/0225274 A1 | 11/2004 | Jansen et al. | |
| 2005/0033260 A1 | 2/2005 | Kubo et al. | |
| 2005/0096627 A1 | 5/2005 | Howard | |
| 2005/0131357 A1 | 6/2005 | Denton et al. | |
| 2005/0230575 A1 | 10/2005 | Zelenski et al. | |
| 2005/0252572 A1 | 11/2005 | Khan et al. | |
| 2005/0252574 A1 | 11/2005 | Khan et al. | |
| 2005/0267413 A1 | 12/2005 | Wang et al. | |
| 2005/0278066 A1 | 12/2005 | Graves et al. | |
| 2006/0048844 A1 | 3/2006 | Merrill | |
| 2006/0064053 A1 | 3/2006 | Bollish et al. | |
| 2006/0169348 A1 | 8/2006 | Yigal | |
| 2006/0178578 A1 | 8/2006 | Tribble et al. | |
| 2006/0259195 A1 | 11/2006 | Eliuk et al. | |
| 2007/0007478 A1 | 1/2007 | Leinsing et al. | |
| 2007/0017583 A1 | 1/2007 | Fangrow | |
| 2007/0088252 A1 | 4/2007 | Pestotnik et al. | |
| 2007/0088313 A1 | 4/2007 | Zinger et al. | |
| 2007/0106244 A1 | 5/2007 | Mosler et al. | |
| 2007/0151984 A1 | 7/2007 | Baker et al. | |
| 2007/0169836 A1 | 7/2007 | Djurle et al. | |
| 2007/0244447 A1 | 10/2007 | Capitaine et al. | |
| 2007/0287953 A1 | 12/2007 | Ziv et al. | |
| 2008/0059228 A1 | 3/2008 | Bossi et al. | |
| 2008/0065006 A1 | 3/2008 | Roger et al. | |
| 2008/0077116 A1 | 3/2008 | Dailey et al. | |
| 2008/0086088 A1 | 4/2008 | Malcom | |

(56)　　　　　References Cited

U.S. PATENT DOCUMENTS

| | | |
|---|---|---|
| 2008/0086094 A1 | 4/2008 | Peters |
| 2008/0114328 A1 | 5/2008 | Doherty et al. |
| 2008/0125897 A1 | 5/2008 | DiGianfilippo et al. |
| 2008/0169043 A1 | 7/2008 | Osborne et al. |
| 2008/0169044 A1 | 7/2008 | Osborne et al. |
| 2008/0172024 A1 | 7/2008 | Yow |
| 2008/0177222 A1 | 7/2008 | Roger |
| 2008/0195416 A1 | 8/2008 | Tribble et al. |
| 2008/0199353 A1 | 8/2008 | Mlodzinski et al. |
| 2008/0269680 A1 | 10/2008 | Ibranyan et al. |
| 2008/0287920 A1 | 11/2008 | Fangrow et al. |
| 2009/0012449 A1 | 1/2009 | Lee et al. |
| 2009/0050216 A1 | 2/2009 | Trocki et al. |
| 2009/0067973 A1 | 3/2009 | Eliuk et al. |
| 2009/0069743 A1 | 3/2009 | Krishnamoorthy et al. |
| 2009/0082649 A1 | 3/2009 | Muller et al. |
| 2009/0088687 A1 | 4/2009 | Yardimci et al. |
| 2009/0099547 A1 | 4/2009 | Radmer |
| 2009/0101576 A1 | 4/2009 | Rohde et al. |
| 2009/0126825 A1 | 5/2009 | Eliuk et al. |
| 2009/0145509 A1 | 6/2009 | Baker et al. |
| 2009/0149743 A1 | 6/2009 | Barron et al. |
| 2009/0154764 A1 | 6/2009 | Khan et al. |
| 2009/0163860 A1 | 6/2009 | Patrick et al. |
| 2009/0177149 A1 | 7/2009 | Childers et al. |
| 2009/0198208 A1 | 8/2009 | Stavsky et al. |
| 2009/0198215 A1 | 8/2009 | Chong et al. |
| 2009/0223592 A1 | 9/2009 | Procyshyn et al. |
| 2009/0223990 A1 | 9/2009 | Bailey et al. |
| 2009/0254031 A1 | 10/2009 | Lee |
| 2009/0270832 A1 | 10/2009 | Vancaillie et al. |
| 2009/0306621 A1 | 12/2009 | Thome, Jr. et al. |
| 2009/0326506 A1 | 12/2009 | Hasegawa et al. |
| 2010/0024904 A1 | 2/2010 | Hoffman et al. |
| 2010/0049157 A1 | 2/2010 | Fangrow |
| 2010/0245056 A1 | 9/2010 | Braun et al. |
| 2010/0276034 A1 | 11/2010 | Gonnelli et al. |
| 2010/0280430 A1 | 11/2010 | Caleffi et al. |
| 2010/0286606 A1 | 11/2010 | Ding |
| 2011/0004143 A1 | 1/2011 | Beiriger et al. |
| 2011/0004187 A1 | 1/2011 | Beiriger |
| 2011/0062703 A1 | 3/2011 | Lopez et al. |
| 2011/0067781 A1 | 3/2011 | Osborne |
| 2011/0152757 A1 | 6/2011 | Beck et al. |
| 2011/0175347 A1 | 7/2011 | Okiyama |
| 2011/0178493 A1 | 7/2011 | Okiyama |
| 2011/0196304 A1 | 8/2011 | Kramer et al. |
| 2011/0204144 A1 | 8/2011 | Waugh et al. |
| 2011/0229517 A1 | 9/2011 | Strahlendorf et al. |
| 2011/0238018 A1* | 9/2011 | McKenzie-Butler ..................... A61M 5/1414 604/257 |
| 2011/0276031 A1 | 11/2011 | Hoang et al. |
| 2011/0305545 A1 | 12/2011 | Davis et al. |
| 2012/0041391 A1 | 2/2012 | Fangrow et al. |
| 2012/0067429 A1 | 3/2012 | Mosler et al. |
| 2012/0109077 A1 | 5/2012 | Ryan |
| 2012/0123298 A1 | 5/2012 | Mendels et al. |
| 2012/0157914 A1 | 6/2012 | Stroup |
| 2012/0298254 A1 | 11/2012 | Brem et al. |
| 2012/0302986 A1 | 11/2012 | Brem et al. |
| 2013/0006214 A1 | 1/2013 | Garfield et al. |
| 2013/0018356 A1 | 1/2013 | Prince et al. |
| 2013/0053815 A1 | 2/2013 | Mucientes et al. |
| 2013/0085439 A1 | 4/2013 | Sansoucy et al. |
| 2013/0102772 A1 | 4/2013 | Eshima et al. |
| 2013/0180618 A1 | 7/2013 | Py |
| 2013/0211332 A1 | 8/2013 | Beiriger et al. |
| 2013/0218121 A1 | 8/2013 | Waller et al. |
| 2013/0220484 A1 | 8/2013 | De Marco |
| 2013/0281965 A1 | 10/2013 | Kamen et al. |
| 2013/0292002 A1 | 11/2013 | Lopez |
| 2013/0292004 A1 | 11/2013 | Ducret et al. |
| 2014/0020790 A1 | 1/2014 | Yuyama et al. |
| 2014/0039392 A1 | 2/2014 | Geipel et al. |
| 2014/0124087 A1 | 5/2014 | Anderson et al. |
| 2014/0124092 A1 | 5/2014 | Gonnelli et al. |
| 2014/0135732 A1 | 5/2014 | Spronken et al. |
| 2014/0136229 A1 | 5/2014 | Levine et al. |
| 2014/0150925 A1 | 6/2014 | Sjogren et al. |
| 2014/0174596 A1 | 6/2014 | Lopez |
| 2014/0261727 A1 | 9/2014 | Mansour et al. |
| 2014/0261860 A1 | 9/2014 | Heath |
| 2014/0261877 A1 | 9/2014 | Ivosevic et al. |
| 2014/0263614 A1 | 9/2014 | Keefe et al. |
| 2014/0276386 A1 | 9/2014 | Mansour et al. |
| 2014/0276649 A1 | 9/2014 | Ivosevic et al. |
| 2014/0299221 A1 | 10/2014 | Lopez |
| 2014/0323970 A1 | 10/2014 | Duncan |
| 2014/0350949 A1 | 11/2014 | Utech et al. |
| 2015/0000784 A1 | 1/2015 | Jamaledine |
| 2015/0008664 A1 | 1/2015 | Tachizaki |
| 2015/0025453 A1 | 1/2015 | Ledford et al. |
| 2015/0040987 A1 | 2/2015 | Reichert et al. |
| 2015/0040988 A1 | 2/2015 | Reichert et al. |
| 2015/0041531 A1 | 2/2015 | Vavala et al. |
| 2015/0045772 A1 | 2/2015 | Reichert et al. |
| 2015/0068640 A1 | 3/2015 | Garfield et al. |
| 2015/0082746 A1 | 3/2015 | Ivosevic et al. |
| 2015/0101707 A1 | 4/2015 | Ranalletta et al. |
| 2015/0119820 A1 | 4/2015 | Kanamoto |
| 2015/0123398 A1 | 5/2015 | Sanders et al. |
| 2015/0126958 A1 | 5/2015 | Sanders et al. |
| 2015/0133879 A1 | 5/2015 | Kanamoto et al. |
| 2015/0151041 A1 | 6/2015 | Yodfat et al. |
| 2015/0157536 A1 | 6/2015 | Qiu et al. |
| 2015/0161354 A1 | 6/2015 | Blomquist |
| 2015/0202382 A1 | 7/2015 | Juretich et al. |
| 2015/0202383 A1 | 7/2015 | Juretich et al. |
| 2015/0202384 A1 | 7/2015 | Juretich et al. |
| 2015/0202385 A1 | 7/2015 | Juretich et al. |
| 2015/0209230 A1 | 7/2015 | Lev et al. |
| 2015/0209233 A1 | 7/2015 | Fukuoka |
| 2015/0209495 A1 | 7/2015 | Biset et al. |
| 2015/0209510 A1 | 7/2015 | Burkholz et al. |
| 2015/0209572 A1 | 7/2015 | Garfield et al. |
| 2015/0250680 A1 | 9/2015 | Browka et al. |
| 2015/0250681 A1 | 9/2015 | Lev et al. |
| 2015/0257977 A1 | 9/2015 | Bochenko et al. |
| 2015/0265500 A1 | 9/2015 | Russo et al. |
| 2015/0297451 A1 | 10/2015 | Mariei et al. |
| 2015/0297453 A1 | 10/2015 | Kim et al. |
| 2015/0297454 A1 | 10/2015 | Sanders et al. |
| 2015/0297456 A1 | 10/2015 | Mariei et al. |
| 2015/0297459 A1 | 10/2015 | Sanders et al. |
| 2015/0297460 A1 | 10/2015 | Mansour et al. |
| 2015/0297839 A1 | 10/2015 | Sanders et al. |
| 2015/0297881 A1 | 10/2015 | Sanders et al. |
| 2015/0314066 A1 | 11/2015 | Shimizu |
| 2015/0320992 A1 | 11/2015 | Bonnet et al. |
| 2015/0346013 A1 | 12/2015 | Feng et al. |
| 2015/0359709 A1 | 12/2015 | Kriheli et al. |
| 2015/0366758 A1 | 12/2015 | Noguchi et al. |
| 2016/0000653 A1 | 1/2016 | Kramer |
| 2016/0001003 A1 | 1/2016 | Perazzo et al. |
| 2016/0038373 A1 | 2/2016 | Ohlin |
| 2016/0038374 A1 | 2/2016 | Merhold et al. |
| 2016/0051446 A1 | 2/2016 | Lev et al. |
| 2016/0058666 A1 | 3/2016 | Strahlendorf et al. |
| 2016/0058667 A1 | 3/2016 | Kriheli |
| 2016/0081878 A1 | 3/2016 | Marks et al. |
| 2016/0081879 A1 | 3/2016 | Garfield et al. |
| 2016/0101020 A1 | 4/2016 | Guala |
| 2016/0114922 A1 | 4/2016 | Bonhora et al. |
| 2016/0136051 A1 | 5/2016 | Lavi |
| 2016/0136412 A1 | 5/2016 | McKinnon et al. |
| 2016/0140315 A1 | 5/2016 | Diaz et al. |
| 2016/0158104 A1 | 6/2016 | Ali et al. |
| 2016/0158437 A1 | 6/2016 | Biasi et al. |
| 2016/0206511 A1 | 7/2016 | Garfield et al. |
| 2016/0213568 A1 | 7/2016 | Mansour et al. |
| 2016/0213861 A1 | 7/2016 | Whitaker et al. |
| 2016/0213862 A1 | 7/2016 | Whitaker et al. |
| 2016/0250102 A1 | 9/2016 | Garfield et al. |

(56) References Cited

U.S. PATENT DOCUMENTS

| | | |
|---|---|---|
| 2016/0256632 A1 | 9/2016 | Fangrow |
| 2016/0262981 A1 | 9/2016 | Carrez et al. |
| 2016/0310362 A1 | 10/2016 | Lane et al. |
| 2016/0331893 A1 | 11/2016 | Yeh et al. |
| 2016/0354281 A1 | 12/2016 | O'Neill et al. |
| 2017/0007501 A1 | 1/2017 | Schuldt-Lieb et al. |
| 2017/0020428 A1 | 1/2017 | Rogers et al. |
| 2017/0079883 A1 | 3/2017 | Lopez |
| 2017/0081168 A1 | 3/2017 | Seay et al. |
| 2017/0128666 A1 | 5/2017 | Davis |
| 2017/0129763 A1 | 5/2017 | Fangrow, Jr. |
| 2017/0146381 A1 | 5/2017 | Eckel et al. |
| 2017/0165435 A1 | 6/2017 | Green |
| 2017/0165436 A1 | 6/2017 | Haddad et al. |
| 2017/0255760 A1 | 9/2017 | Lee et al. |
| 2017/0312716 A1 | 11/2017 | Konrad, Jr. et al. |
| 2017/0354571 A1 | 12/2017 | David et al. |
| 2018/0028403 A1 | 2/2018 | Fangrow |
| 2018/0043323 A1 | 2/2018 | Janders et al. |
| 2018/0055738 A1 | 3/2018 | Chen et al. |
| 2018/0065097 A1 | 3/2018 | Konrad, Jr. et al. |
| 2018/0133667 A1 | 5/2018 | Lee et al. |
| 2018/0161244 A1 | 6/2018 | Lopez |
| 2018/0168930 A1 | 6/2018 | Tunesi |
| 2018/0168935 A1 | 6/2018 | Chen et al. |
| 2018/0177940 A1 | 6/2018 | Hachey et al. |
| 2018/0194505 A1 | 7/2018 | Amano et al. |
| 2018/0207063 A1 | 7/2018 | Lopez |
| 2018/0232497 A1 | 8/2018 | Hoffman et al. |
| 2018/0263850 A1 | 9/2018 | Schneider et al. |
| 2018/0272117 A1 | 9/2018 | Fangrow |
| 2018/0344572 A1 | 12/2018 | Zollinger et al. |
| 2018/0353381 A1 | 12/2018 | Pak et al. |
| 2018/0353382 A1 | 12/2018 | Zollinger et al. |
| 2018/0354662 A1 | 12/2018 | Feith et al. |
| 2018/0357476 A1 | 12/2018 | Klumph |
| 2018/0360689 A1 | 12/2018 | Zollinger et al. |
| 2019/0019576 A1 | 1/2019 | DeCiccio et al. |
| 2019/0021947 A1 | 1/2019 | Bomgaars et al. |
| 2019/0056419 A1 | 2/2019 | Procyshyn et al. |
| 2019/0070405 A1 | 3/2019 | Fangrow |
| 2019/0091639 A1 | 3/2019 | Brown et al. |
| 2019/0105619 A1 | 4/2019 | Wilson et al. |
| 2019/0151569 A1 | 5/2019 | Fangrow et al. |
| 2019/0152663 A1 | 5/2019 | Kraft |
| 2019/0163876 A1 | 5/2019 | Remme et al. |
| 2019/0170663 A1 | 6/2019 | Pirkle et al. |
| 2019/0216683 A1 | 7/2019 | Yaegashi |
| 2019/0244466 A1 | 8/2019 | Berg et al. |
| 2019/0247280 A1 | 8/2019 | Hellenbrand |
| 2019/0262790 A1 | 8/2019 | Konrad, Jr. et al. |
| 2019/0275243 A1 | 9/2019 | Deck et al. |
| 2019/0307643 A1 | 10/2019 | Tribble et al. |
| 2019/0388302 A1 | 12/2019 | Schobel et al. |
| 2020/0016037 A1 | 1/2020 | Oda et al. |
| 2020/0066389 A1 | 2/2020 | Prince et al. |
| 2020/0093699 A1 | 3/2020 | Oda et al. |
| 2020/0113784 A1 | 4/2020 | Lopez et al. |
| 2020/0113785 A1 | 4/2020 | Lopez |
| 2020/0206492 A1 | 7/2020 | Fangrow |
| 2020/0289370 A1 | 9/2020 | Lopez |
| 2020/0297581 A1 | 9/2020 | Lopez et al. |
| 2021/0002008 A1 | 1/2021 | Min et al. |
| 2021/0121363 A1 | 4/2021 | Oda et al. |
| 2021/0259921 A1 | 8/2021 | Lopez |
| 2021/0308012 A1 | 10/2021 | Tagliamento |
| 2022/0008711 A1 | 1/2022 | Fangrow |
| 2022/0054766 A1 | 2/2022 | Fangrow et al. |
| 2022/0379697 A1 | 12/2022 | Lopez |
| 2024/0382738 A1 | 11/2024 | Fangrow |
| 2025/0099334 A1 | 3/2025 | Lopez |
| 2025/0161590 A1 | 5/2025 | Fangrow |
| 2025/0228744 A1 | 7/2025 | Lopez |

FOREIGN PATENT DOCUMENTS

| | | |
|---|---|---|
| CN | 106860003 A | 6/2017 |
| CN | 107198658 A | 9/2017 |
| CN | 108210332 A | 6/2018 |
| DE | 202 16 791 U | 2/2003 |
| DE | 20 2004 014 868 | 11/2004 |
| EP | 0 577 354 | 1/1994 |
| EP | 0 521 460 B1 | 9/1995 |
| EP | 0 974 330 | 1/2000 |
| EP | 1 533 597 | 5/2005 |
| EP | 1 563 819 | 8/2005 |
| EP | 1 997 471 | 12/2008 |
| EP | 3 375 427 A1 | 9/2018 |
| JP | S55-156750 | 11/1980 |
| JP | 55-173339 | 12/1980 |
| JP | 56-95247 A | 8/1981 |
| JP | 62-189072 A | 8/1987 |
| JP | 06-343706 | 12/1994 |
| JP | 10-118158 A | 5/1998 |
| JP | 2001-190689 A | 7/2001 |
| JP | 2002-238979 A | 8/2002 |
| JP | 2002-355318 | 12/2002 |
| JP | 2003-144546 | 5/2003 |
| JP | 2003-199823 | 7/2003 |
| JP | 2003-225305 A | 8/2003 |
| JP | 2004-049497 | 2/2004 |
| JP | 2007-14618 A | 1/2007 |
| JP | 2007-215775 A | 8/2007 |
| KR | 2011-0019800 | 3/2011 |
| KR | 10-1574194 B1 | 12/2015 |
| WO | WO 1997/14493 | 4/1997 |
| WO | WO 1998/23353 | 6/1998 |
| WO | WO 1999/19012 | 4/1999 |
| WO | WO 1999/63547 | 12/1999 |
| WO | WO 2000/41751 | 7/2000 |
| WO | WO 2001/03757 | 1/2001 |
| WO | WO 2001/039874 | 6/2001 |
| WO | WO 2002/013890 | 2/2002 |
| WO | WO 2005/041846 | 5/2005 |
| WO | WO 2005/110007 | 11/2005 |
| WO | WO 2005/123162 | 12/2005 |
| WO | WO 2007/033013 | 3/2007 |
| WO | WO 2007/061424 | 5/2007 |
| WO | WO 2007/062315 | 5/2007 |
| WO | WO 2007/079305 | 7/2007 |
| WO | WO 2007/148708 | 12/2007 |
| WO | WO 2008/051998 | 5/2008 |
| WO | WO 2008/128074 | 10/2008 |
| WO | WO 2008/144447 | 11/2008 |
| WO | WO 2009/060419 | 5/2009 |
| WO | WO 2009/130147 | 10/2009 |
| WO | WO 2011/002853 | 1/2011 |
| WO | WO 2011/012313 | 2/2011 |
| WO | WO 2011/014525 | 2/2011 |
| WO | WO 2011/058545 | 5/2011 |
| WO | WO 2011/058548 | 5/2011 |
| WO | WO 2011/091542 | 8/2011 |
| WO | WO 2011/091543 | 8/2011 |
| WO | WO 2011/104711 | 9/2011 |
| WO | WO 2011/104712 | 9/2011 |
| WO | WO 2011/150037 | 12/2011 |
| WO | WO 2012/119225 | 9/2012 |
| WO | WO 2013/096911 | 6/2013 |
| WO | WO 2014/122643 | 8/2014 |
| WO | WO 2014/126473 | 8/2014 |
| WO | WO 2014/177347 | 11/2014 |
| WO | WO 2014/181320 | 11/2014 |
| WO | WO 2015/029020 | 3/2015 |
| WO | WO 2015/077184 | 5/2015 |
| WO | WO 2015/077466 | 5/2015 |
| WO | WO 2015/122921 | 8/2015 |
| WO | WO 2016/010909 | 1/2016 |
| WO | WO 2017/096072 | 6/2017 |
| WO | WO 2018/009996 | 1/2018 |
| WO | WO 2018/022640 | 2/2018 |

(56)                    References Cited

FOREIGN PATENT DOCUMENTS

WO      WO 2019/018195      1/2019
WO      WO 2021/201884      10/2021

OTHER PUBLICATIONS

U.S. Appl. No. 29/586,575, filed Dec. 5, 2016, Fangrow.
Abbott "Plum A+," System Operating Manual (For use with List 11971-04) in 85 pages, May 2001.
Autoyec 50, from KRZ, Dec. 6, 2007.
B. Braun Medical Inc. Two-Bag Irrigation Set, Two Non-vented Spikes, dated Jul. 2012, in 1 page.
*Baxa Corp.* v. *McGaw Inc.* 981 F. Supp. 1348 (1997), Memorandum Opinion and Order, 14 pages.
BioExpert International Inc., Company overview, credentials for Rabih Jamaleddine, Nabil Kereknawi, and Danica Robillard Corso, copyright 2010 BioExpert International Inc. in 3 pages [retrieved on Jan. 6, 2015; Publication Date Unknown]; accessed on the world wide web at http://bioexpert.ca/about.html.
Burrows, et al., "Intravenous (IV) Fluidmaker IV. A Disposable Device for Preparation of Sterile Water for Injection in a Field Setting," Fort Detrick, US Army Biomedical Research & Development Laboratory, Sep. 1991. https://apps.dtc.mil/dtic/tr/fulltest/u2/a247385.pdf.
Cato (Computer Aided Therapy for Oncology)—Reference Manual—Vienna, May 2005, 255 pgs.
Clearlink Needleless IV Access System, dated Aug. 2007, in 2 pages.
CytoCare, by Health Robotics, Brochure, Date Unknown, downloaded on May 25, 2012 from http://www.health-robotics.com/smartedit/downloads/en/cytocare7.pdf, 6 pages.
European Supplemental Search Report, re EP Application No. 14864639, dated May 12, 2017.
Exacta-Mix 2400, from Baxa, which appears to have a date of 2007, 2 pages.
Flickinger, Bruce, "Misperceptions Cloud the Issue of Sterile Drug Compounding," Jun. 2007.
Fox, Brent I., "Pharmacy Automation and Technology: Automated Intravenous Preparation: Robots for the Pharmacy," Hospital Pharmacy, vol. 44, Mar. 2009, pp. 255-257.
Grifols International, S.A., "Phocus Rx, Remote IV Compounding Validation" product brochure and "Product Description Sheet" in 13 pages [Publication Date unknown but may be May 29, 2013].
Healthmark, "Hospital Medication Preparation, Packaging and Dispensing" in 1 page [retrieved on Jan. 6, 2015; Publication Date Unknown]; accessed on the world wide web at http://www.healthmark.ca/2-en-Hospital-Medication-Preparation-Packaging-and-Dispensing.html.
Healthmark, "Hospital Medication Preparation, Packaging and Dispensing," Chemo Drug Preparation/Administration in 2 pages [retrieved on Jan. 6, 2015; Publication Date Unknown]; accessed on the world wide web at http://www.healthmark.ca/2-36-88-Chemo-Drug-Preparation-Administration_en.html.
Healthmark, "Hospital Medication Preparation, Packaging and Dispensing," Chemosphere, Sterile Chemo Compounding (Isolator) in 1 page [retrieved on Jan. 6, 2015; Publication Date Unknown]; accessed on the world wide web at http://www.healthmark.ca/2-36-10-ChemoSphere_en.html?ProductID=244.

Healthmark, "Hospital Medication Preparation, Packaging and Dispensing," Oncology Preparation and Administration in 1 page [retrieved on Jan. 6, 2015; Publication Date Unknown]; accessed on the world wide web at http://www.healthmark.ca/2-36-10-COMPANY-PROFILEHospital-en.html.
Healthmark, "Hospital Medication Preparation, Packaging and Dispensing, "Phocus—RX (Camera Verification System), Remote Rx Checking of admixtures in 2 pages [retrieved on Jan. 6, 2015; Publication Date Unknown]; accessed on the world wide web at http://www.healthmark.ca/2-10-PHOCUS-Rx-Camera-Verification-System-_en.html?ProductID=229.
Healthmark, "New Product Items" in 1 page [retrieved on Jan. 6, 2015; Publication Date Unknown]; accessed on the world wide web at http://www.healthmark.ca/home.html.
Healthmark, "Introducing the Precifill Dispensing Pump" product brochure in 2 pages [Publication Date Unknown].
Integra Brochure, from Eurospital, Brochure acquired in Mar. 2012.
International Preliminary Report on Patentability for International PCT Patent Application No. PCT/US2014/065972, mailed Jun. 9, 2016.
International Search Report and Written Opinion for International PCT Patent Application No. PCT/US2014/065972, dated Feb. 24, 2015.
ISO/Tech Design, QC, Canada, "ChemoSphere," product brochure, in 2 pages [Publication Date Unknown].
Neo Care Medical Products: Product Catalog, dated Jun. 2008, in 38 pages.
Pinnacle TPN Management System, from B Braun, downloaded May 5, 2009 from http://www.bbraunusa.com/index. cfm?uuid=7386ADF065B05CD0D22AF700339AA4092, 1 page.
"Precifill," Trademark search (TESS) in 1 page, [retrieved on Jan. 6, 2015; Application Filing Date of Sep. 30, 2011].
Product detail for "NAMIC® Closed Fluid Systems" from Navilyst Medical, downloaded on May 11, 2010 from http://www.navilystmedical.com/Products/index.cfm/19, 2 pages.
Product detail for "RapidFill™Automated Syringe Filler," from Baxa, downloaded on Mar. 31, 2010 from http://www.baxa.com/PharmacyProducts/AutomatedFillingSystems/ProductDetail/?id=B1, 2 pages.
Product detail for "Summit Medical DirectFlow" micro infusion extension set from Summit Medical Technologies, downloaded on May 10, 2010 from http://summitmedtech.com/p6line.php, 1 page.
Riva, downloaded in Apr. 2009 from http://www.rivasystem.com, 6 pages.
SmartSite Safety Disposables, with copyright notice dated 2004.
Smith, "Lifesaving Cancer Drugs May Put Workers' Lives at Risk," downloaded on Jul. 12, 2010 from http://www.msnbc.msn.com/id/38114586/ns/health-cancer, 7 pages.
Spiros—Closed Male Connector, published Jan. 22, 2008.
Technical Data sheet for Analog Amplifiers Type VA, models V8-C and V8-D, STM Sensors dated Dec. 2007, 4 pages.
Technical Data sheet for Through Beam Sensors Type G2, 1480 nm, STM Sensors dated Dec. 2009, 2 pages.
Technical Data sheet for Through Beam Sensors Type G2, 645 nm, STM Sensors dated Sep. 2008, 2 pages.
User Guide for medOC 1xx Basic, Neo Care Medical Products GmbH, Version Jun. 2008, 23 pages.
User Manual for medOC 3xx /6xx /8xx, Neo Care Medical Products GmbH, Version May 2008, 44 pages.

* cited by examiner

METHODS AND SYSTEMS FOR FILLING IV BAGS WITH THERAPEUTIC FLUID

RELATED APPLICATIONS

This application is a continuation application of U.S. patent application Ser. No. 15/848,368, filed Dec. 20, 2017, and issued as U.S. Pat. No. 11,541,171 on Jan. 3, 2023, which is a continuation application of U.S. patent application Ser. No. 14/746,048, filed Jun. 22, 2015, and issued as U.S. Pat. No. 9,849,236 on Dec. 26, 2017, which claims the benefit under 35 U.S.C. § 120 and 35 U.S.C. § 365(c) as a continuation of International Application No. PCT/US2014/065972, designating the U.S., with an international filing date of Nov. 17, 2014, entitled "Methods and Systems for Filling IV Bags with Therapeutic Fluid," which claims the benefit of U.S. Provisional Patent Application No. 61/908,674, filed on Nov. 25, 2013, and entitled "Method and Systems for Filling IV Bags with Therapeutic Fluid." The entirety of each of the above-mentioned applications is hereby incorporated by reference herein and made a part of this disclosure.

BACKGROUND

Field

This invention relates generally to medical fluid systems, and specifically to systems for providing IV fluid to patients.

Related Art

In a typical hospital setting, when a patient is in need of intravenous fluid therapy, a healthcare practitioner: (i) obtains a pre-filled IV bag that has a large port with a flexible septum; (ii) wipes an antiseptic pad across the septum; and (iii) pierces the septum of the bag with a large, hollow spike. The septum forms a seal around the spike. The spike is connected to empty medical tubing, which in turn may be connected to a fluid connector.

The medical tubing is configured to convey medical fluid from the IV bag to the patient; however, before the tubing can be connected in fluid communication with the patient, it must be "primed" with liquid to avoid introducing air or vapors from the liquid into the patient's vasculature, which could be very harmful. To prime the tubing, the healthcare practitioner positions the IV bag at a higher location than the tubing, and sometimes squeezes the IV bag, permitting gravity and liquid pressure to drive the liquid in the IV bag downward in a column through the tubing, pushing the air and vapors in the tubing out the bottom end of the tubing. When the column of liquid reaches the bottom end of the tubing, a small amount of liquid is typically permitted to drip out of the end of the tubing, or out of the end of a connector attached to the end of the tubing, into a trashcan or sink, to ensure that no residual air or vapors remain in the fluid line.

The process of spiking the IV bag and priming the fluid line requires significant time and attention from the healthcare practitioner at the patient care site, and also requires that multiple components be inventoried at the patient care site. In addition, there are many inherent disadvantages with the bag-spiking process. The tip of the spike is sharp and can inadvertently puncture the healthcare provider or patient. The spike or the septum of the spike port can carry microbes, if not properly disinfected, that may be introduced into the IV fluid when attached. The connection between the spike and spike port may leak if connected improperly. Also, the priming process can permit a small amount of vapors and liquid to escape, which can be dangerous, especially if the liquid is potential harmful, such as chemotherapy or immunosuppressive drugs.

Moreover, in many healthcare treatment settings, a large number of IV bags need to be filled with customized amounts and types of drugs on a daily basis for many different patients. If performed manually, this repetitive task is susceptible to mistakes by healthcare technicians. It can also continuously expose healthcare technicians to harmful medicinal vapors, and it can be a physically difficult chore for a healthcare technician, especially when using a large-diameter filling syringe in which the syringe plunger is especially wide and hard to push forward and back.

SUMMARY OF SOME EMBODIMENTS OF THE DISCLOSURE

In some embodiments, a portable electronic fluid dispensing system can provide pre-filled, pre-primed IV bag assemblies comprising therapeutic fluids in particular amounts and/or particular concentrations that are custom-made for a particular patient. The IV bag assembly in some embodiments can form a part of a substantially entirely closed fluid system. The same fluid line and connector in the IV bag assembly can be used to fill the IV bag as is used to withdraw fluid from the IV bag and infuse such fluid into the patient. The connection points along the IV assembly, such as the connection between the IV bag and a drip chamber, or between an IV bag and tubing, or between a drip chamber and tubing, or between tubing and a closeable, resealable connector, can each be resistant to disconnection by a user. In some embodiments, the healthcare practitioner at the patient care site is not required to attach any of these components to each other, and/or the healthcare practitioner at the patient care site is not required to introduce a spike into a spike port on the IV bag.

DETAILED DESCRIPTION OF SOME EMBODIMENTS

The components, systems, assemblies, and methods that are illustrated or described in this specification are examples. Any component, structure, feature, or step illustrated or described in one embodiment can be used in additional to or instead of any component, structure, feature, or step illustrated or described in another embodiment. There is no component, structure, feature, or step in this specification that is essential or indispensable to the invention.

Figure 1A:
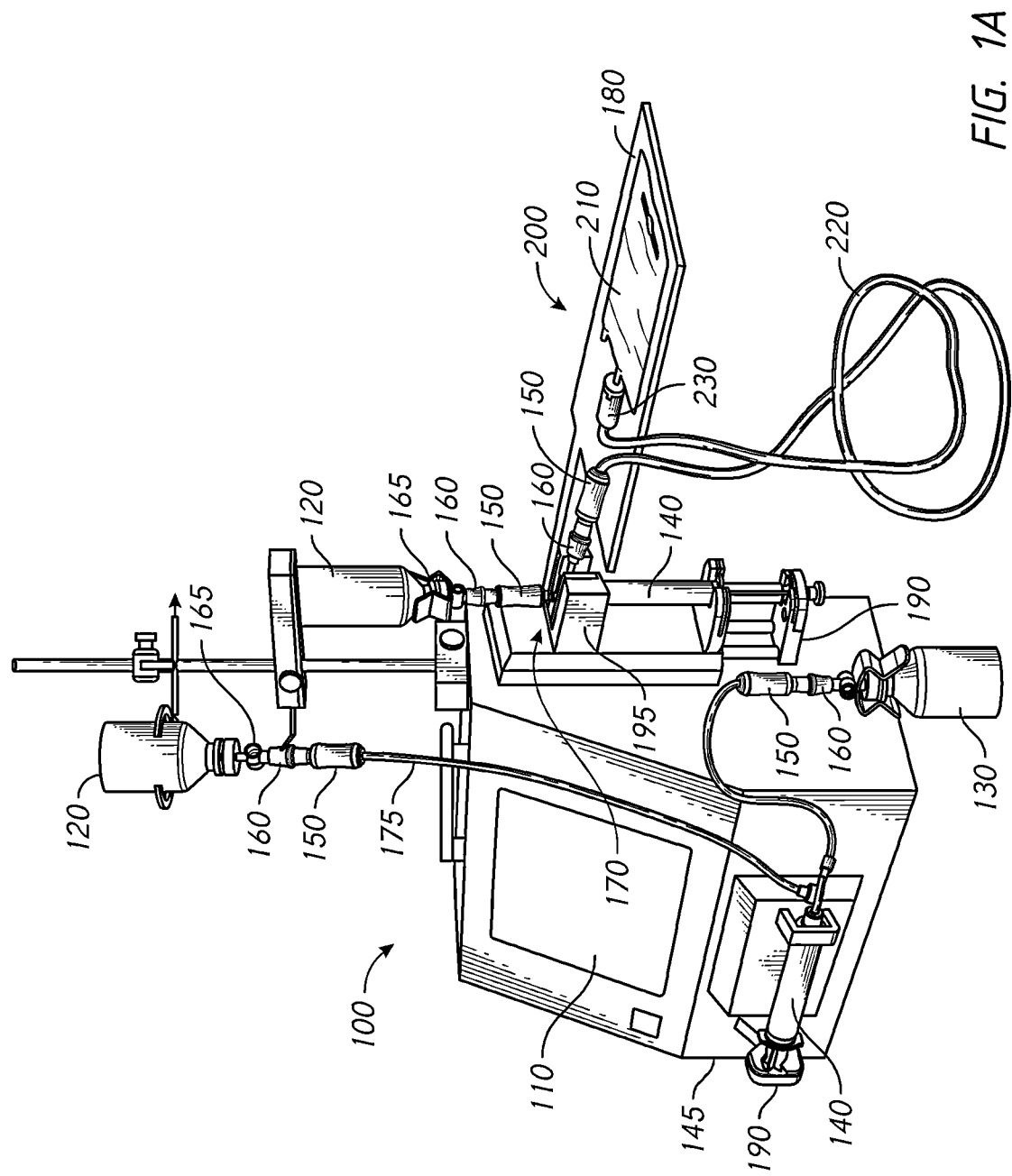
FIG. 1A is a perspective view of a portable electronic medical fluid dispensing system in fluid communication with an example of an IV assembly comprising an integral liquid delivery path.
Figure 1B:
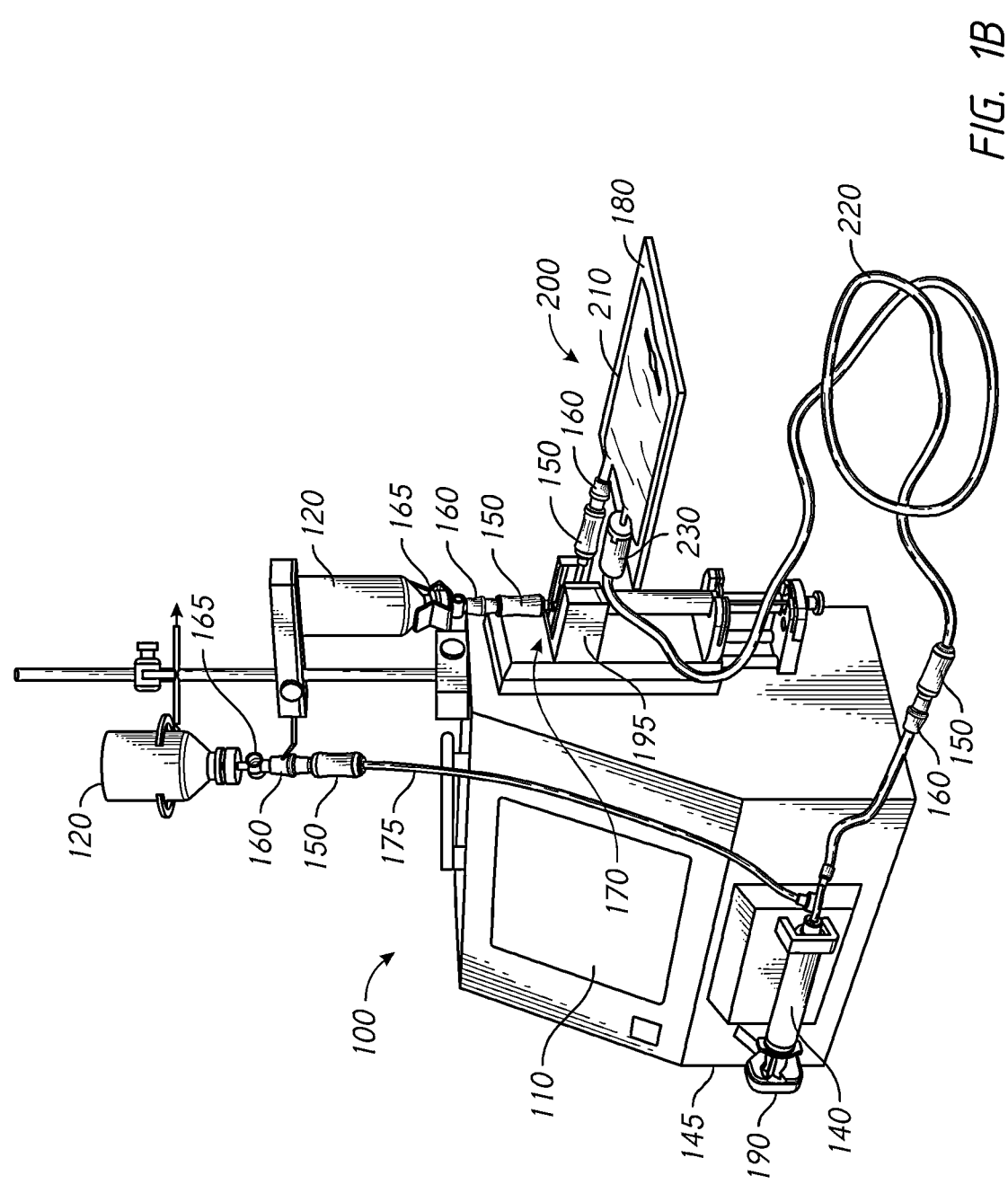
FIG. 1B is a perspective view of the electronic medical fluid dispensing system of FIG. 1A in fluid communication with another example of an IV assembly comprising an integral liquid delivery path.

As shown in FIGS. 1A and 1B, an electronic fluid delivery system 100 can comprise an external housing 145 containing or supporting various internal components, such as a power regulator, a microprocessor, a drive motor, a driving mechanism (e.g., gearing), a memory, and communications hardware and software to enable electronic communication with a network or with one or more peripheral devices, such as a printer to produce a label or a report with information about a particular fluid delivery process that has been performed. The electronic fluid delivery system 100 can also comprise an electronic display and/or a user input system 110, one or more replaceable liquid source containers 120 filled with medical liquid (such as liquid medical vials as shown), one or more liquid pumps and/or liquid measurers 140 (such a syringe pump as shown), and/or one or more drive systems 190 functionally coupled to the liquid pumps and/or liquid measurers 140.

The electronic fluid delivery system 100 can be configured to receive one or more commands from a user through the user input system 100, or in some other way. The user command or commands can initiate a delivery of a particular type of one or more medications in a particular volume or concentration. Upon receiving a liquid delivery command, the electronic fluid delivery system 100 can cause the drive system 190 to actuate the liquid pump and/or measurer 140 to withdraw an amount of liquid from a liquid source container 120, move it through a fluid pathway or channel in the electronic fluid delivery system 100, and push it into a fluid destination container, such as an IV assembly 200, as shown. The fluid pathway or channel can comprise a number of different structures of the electronic fluid delivery system 100 through which liquid passes as it progresses from the liquid source container 120 to the fluid destination container 200.

An adapter, such as a vial adapter 165, as shown, can provide an interface between the liquid source container 120 and the fluid channel. The adapter can comprise a hollow spike (not shown) for penetrating a septum on a liquid vial to access the liquid contained in the vial. In some embodiments, a plurality of different liquid source containers 120, fluid channels, pumps, and/or liquid destination containers 130, 210 can be provided. In some embodiments, a plurality of different liquid source containers 120 with different medical fluids, such as different types of drugs, can be available to infuse in a specified combination into the same destination container 130, 210.

In some embodiments, a support 180 can be provided for supporting a liquid destination container. As illustrated, the support 180 can be oriented in a substantially horizontal position, but many other types of supports can be used, including substantially vertical supports such as hangers. The support 180 can provide a platform and/or a location to hold onto or secure an IV assembly 200 comprising an IV bag 210, a drip chamber 230, a tubing 220, and a fluid-line connector, such as a closeable male luer connector 150, as shown.

The IV assembly 200 can be removably attached to and/or in fluid communication with the fluid pathway or channel in the electronic fluid delivery system 100, which can include one or a plurality of an adapter, a pump, a connector (such as a resealable, needleless male or female luer connector 150, 160), tubing, and a removable, disposable fluid transfer cartridge 170. None of the foregoing components is essential or indispensable; rather, various other types of components can be used instead of or in addition to those listed. For example, in some embodiments, an open-ended male or female fluid connector can be used instead of a resealable, needleless connector, especially in embodiments involving benign fluids with clamps or stop-cocks in the fluid line. Various components of the fluid channel in the electronic fluid delivery system 100 can be removed and replaced, such as the liquid source container 120, the IV assembly 200, the syringe pump 140, and the cartridge 170, which can each form a portion of the fluid channel when attached. Each of these components can form a repeatably resealable connection with the fluid channel, and when detached from the fluid channel, each of these components can comprise a sealed end that prevents conveyed or residual fluid from leaking out after disconnection. The resealable connections at each point of removable attachment in the fluid channel can be made using a series of male and female needleless luer connectors 150, 160.

The electronic fluid delivery system 100 can be positioned in a fume hood and the fluid transfer can be performed in the fume hood; however, in some embodiments, as shown, any fumes and fluid are maintained inside of a closed system, so it is not required to use the system 100 in a fume hood. In some embodiments, fluid progresses under the influence of back and forth motion of the fluid pump 140, in a substantially closed system from a liquid source container 120, through the fluid channel of the electronic fluid transfer cartridge 170, and to the fluid destination container 200, which substantially entirely prevents liquids and vapors from escaping during fluid transfer. As used herein, unless otherwise indicated, the terms "substantially entirely prevents," or "substantially entirely closed" or "substantially entirely closed system" and related or similar terms refer to processes and systems in which vapors and liquids are maintained inside a bounded region during normal usage and operating conditions to the degree that it is needed to avoid clinically significant adverse effects on healthcare practitioners or patients. Also, in some embodiments, each removable component (such as the cartridge 170, or the source container 120 and vial adapter 165, or the IV assembly 200) that temporarily forms part of, or that is temporarily attached to, the fluid channel in the electronic fluid transfer system 100 can separately form a resealable, substantially entirely closed fluid system within itself, which substantially entirely prevents liquids and vapors from escaping during fluid transfer, and which can dramatically lower or eliminate the amount and frequency of exposure of healthcare practitioners to harmful liquids and vapors during preparation and transfer of harmful fluids.

The fluid transfer cartridge 170 can comprise a disposable portion of the fluid channel of the electronic fluid delivery system 100 that selectively directs fluid out of one or more fluid source containers 120 and into one or more fluid destination containers 210. The fluid transfer cartridge 170 may include one or more internal valves (not shown) to permit liquid to move in one direction away from a fluid source container 120 and toward a fluid destination container 210, while resisting unintended flow in an opposing direction. As illustrated, the fluid transfer cartridge 170 can comprise one or more closeable, resealable, needleless connectors, such as closeable male and female connectors 150, 160, that are configured to connect to other portions of the fluid channel within the electronic fluid delivery system, such as an adapter on the fluid source container 120 and a connector on the fluid destination container 210. The fluid transfer cartridge can be supported or held in place by a holder 195. As used in this specification, unless otherwise specified, the terms "connect," "attach," "hold," and related or similar terms are contemplated in a broad sense to refer to structures that are joined together, either directly or indirectly, to each other or to a common structure, and these terms can encompass parts that are either separable or integral with each other.

In some embodiments, as illustrated, the electronic fluid delivery system 100 can comprise multiple fluid pathways or channels for delivering different types of medicinal liquids. For example, a first pathway or channel can be configured to supply a first type of liquid (e.g., an inert or benign liquid such as water, saline solution, electrolyte liquid, or other diluent) from a first liquid source container 120, through a first fluid line 175, through a first pump or measurer 140, to a first fluid destination container 130, and a second pathway or channel can be configured to supply a second type of liquid (e.g., one or more drugs or combinations of drugs, such as a chemotherapy drug, an antibiotic, an immunosuppressive drug, and/or a pain management drug, etc.) from a second liquid source container 120, through a second fluid pathway to a second pump or measurer 140, to a second fluid destination container, such as the IV assembly 200. In some embodiments, both the first and second fluid pathways or channels can be used to fill the same fluid destination container, such as the IV assembly 200, either serially or in parallel, and/or through the same fluid port on the fluid destination container, or through multiple, different fluid ports on the same fluid destination container.

Figure 2:
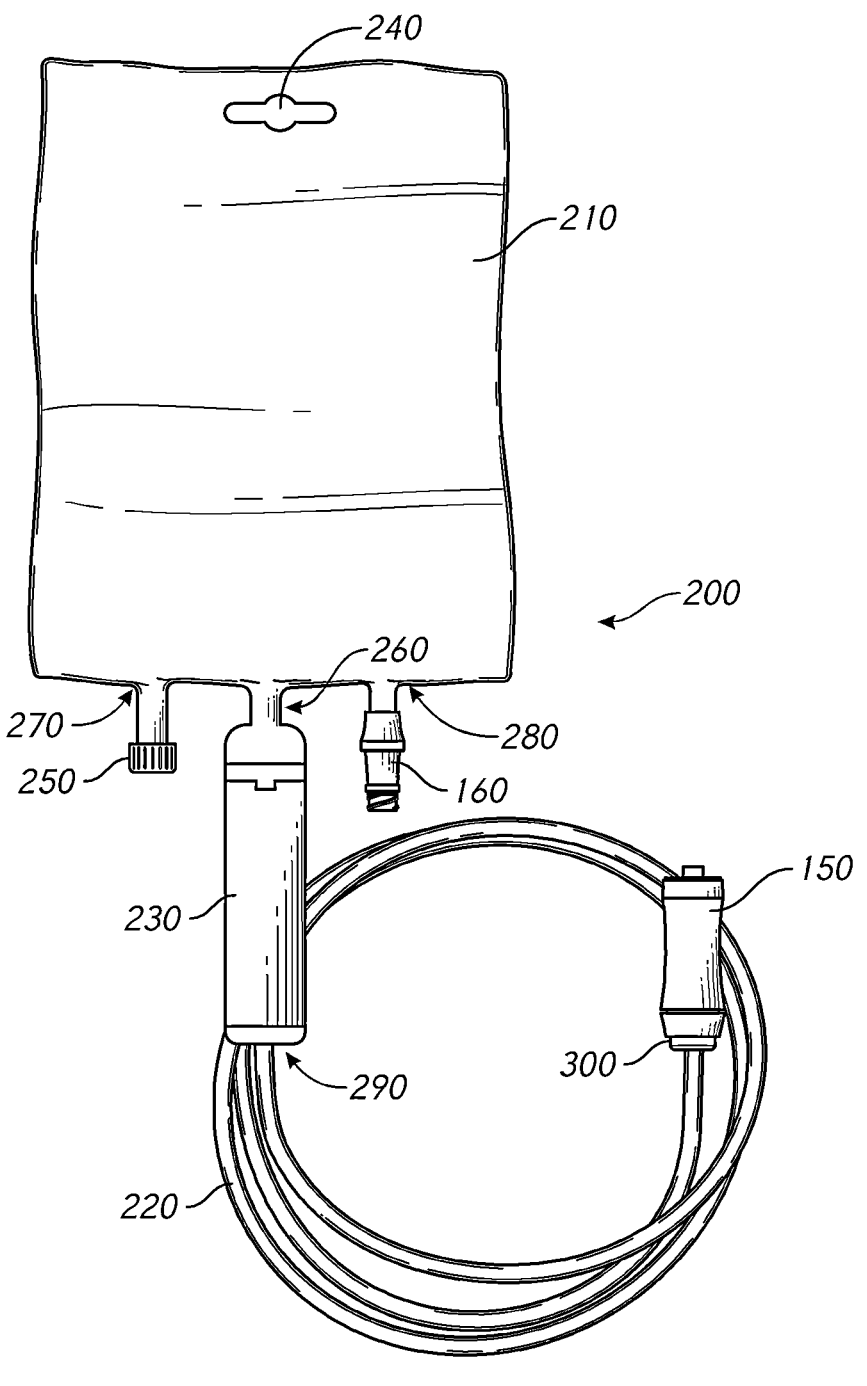
FIG. 2 is a top view of the IV assembly with an integral liquid delivery path as shown in FIG. 1.

Referring to FIG. 2, an example of a fluid destination container in the form of an IV assembly 200 is illustrated. Many other types or configurations of IV assemblies, and many other types or configurations of fluid destination containers, can be used in addition to or instead of the illustrated embodiment. Any reference in this specification to an IV bag or an IV assembly should be understood to also refer to and be applicable to any other type of fluid destination container, including but not limited to any bottle, vial, cartridge, syringe, chamber, bag, tank, or other enclosure. In its initial state, the IV assembly 200 comprises an empty, substantially flat IV bag 210 that can be formed in some embodiments by two layers of flexible plastic joined along substantially their entire peripheries, a long tubing 300, and a closeable needleless connector (if used), such as a closeable male luer connector 150, as illustrated. In some embodiments, as shown, the IV assembly 200 can comprise one or more additional fluid-line ports (if used), including one or more input or output ports, such as a needleless closeable female luer connector 160 and/or a pierceable septum connector 250, either or both of which can be configured to permit fluid to be added to or removed from the IV bag 210 by attaching another medical implement, such as a syringe or connector, to either or both of the input or output ports. The one or more additional fluid ports can be configured to permit filling of the IV assembly 200 with different types of liquids through different ports of the IV assembly 200. For example, a first type of fluid, such as one or more active or potentially harmful therapeutic fluids (e.g., chemotherapy drugs or immunosuppressive drugs), can be infused through a first port 160, and a second type of fluid, such as one or more inert or benign liquids (e.g., water, saline, or other diluent), can be infused through a second fluid pathway, such as the connector 150 and tubing 220. However, in some embodiments, all liquids can be passed into and out of the IV assembly 200 through a single fluid line and connector.

In some cases, if the fluids are passed through a single fluid line and connector, different types of fluids can be used to fill the IV assembly 200 in series (e.g., first the active drugs and/or potentially harmful drugs, and second the benign liquids such as water, saline, or other diluent). In some cases, if the fluids are passed through different fluid lines and connectors, different types of fluids can be used to fill the IV assembly 200 in parallel or generally simultaneously, and such an arrangement can in some embodiments accomplish the filling in a shorter amount of time. Further, in some cases, filling different drugs through different ports in the same IV assembly 200 can help to achieve a more thorough mixing and generally uniform dilution and concentration of the liquids in the IV bag. Also, when the active or potentially harmful drugs are passed through the alternative or non-patient infusion line 160, 250, parallel infusion can help to avoid positioning harmful drugs in the leading fluid connector 150 or infusion fluid tubing 220 during transportation and initial opening of the fluid line in the IV assembly at the patient care site. In some embodiments, as shown, the IV assembly 200 can comprise a drip chamber 230 in the patient infusion fluid line.

In the illustrated embodiment, the drip chamber 230 is connected, or bonded directly, permanently, and irreversibly, to a bottom opening in the IV bag 210 at the IV bag-drip chamber bond 260, the long tubing 300 is connected, or bonded directly, permanently, and irreversibly, to a bottom opening in the drip chamber 230 at the drip chamber-tubing bond 290, and a needleless closeable connector, such as a closeable male luer connector 150 or a closeable female luer connector (not shown in FIG. 2), is connected, or bonded directly, permanently, and irreversible to a bottom end of the long tubing 220 at the tubing-connector bond 300. In some embodiments, the long tubing 300 is connected, or bonded directly, permanently, and irreversibly, to a bottom opening in the IV bag 210, without a drip chamber 230. Either or both of the additional fluid-line ports can be bonded directly, permanently, and irreversibly to bottom openings in the IV bag 210 at the IV bag-pierceable septum connector bond 270 and/or at the IV bag-connector bond 280. The bonding at any of the bonding regions 260, 270, 280, 290, 300 can be accomplished in any suitable manner, such as using adhesive, solvent, ultrasonic welding, thermoforming, heat staking, one-way screwing attachment, snap-fit, interference fit, etc. In some embodiments, the permanence of these bonds helps to achieve a closed system and to diminish the risk of entry of microbes into the IV line and to diminish the risk of exposure of dangerous fluids or vapors to healthcare practitioners and patients. The permanence of these bonds can help to avoid inadvertent removal or pulling out of a fluid line (such as by tugging on a bag spike that has been inserted through a bag port). In some embodiments, one or more of the connection points between any of these components 210, 230, 220, 150 can comprise a rotating or swiveling connection to help avoid tangling or kinking of the tubing 220.

In some embodiments, the tubing 220 can be sufficiently long so as to extend comfortably, without creating a disruptive degree of fluid-line tension and without unduly constraining the patient's movement, from a typical position on or near the IV bag 210 in a hanging position on an IV pole (see FIG. 4) or other holder to a region near a fluid pump or near a patient in a lying position on a standard hospital bed, such as at an attachment point with another fluid connector (e.g., a needleless closeable female luer connector 160), that is attached to a fluid line that extends into the patient. In some embodiments, the tubing is at least about 2½ feet (30 inches) long, or least about 3 feet (36 inches) long, or between about 2½ feet long and about 3½ feet long, or between about 30 inches long and about 100 inches long. In some embodiments, the tubing can be formed from an extruded, continuous, homogeneous material, with substantially the same thickness, durometer, flexibility, diameter, and/or tension strength from one end of the tubing to the other end of the tubing or from the connection point at the IV bag 210 or drip chamber 230 to the resealable connector 150.

As illustrated, in some embodiments, the fluid pathway within the IV assembly 200 is configured to be open and in continuous fluid communication from a location within the IV bag 210, through the drip chamber 230 and/or tubing 220, to the closeable connector 150, without any blockage, valve, obstruction and/or resistance to fluid flow. In some embodiments, the fluid pathway in the IV assembly 200 is integral: the connections between the components forming the fluid pathway within the IV assembly 200, from a location within the IV bag 210, through the drip chamber 230 and/or tubing 220, to the closeable connector 150, are configured to be permanent and/or to resist disconnection by a user at any point within the fluid delivery pathway within the IV assembly 200 from the IV bag 210 to the patient.

Figure 3:
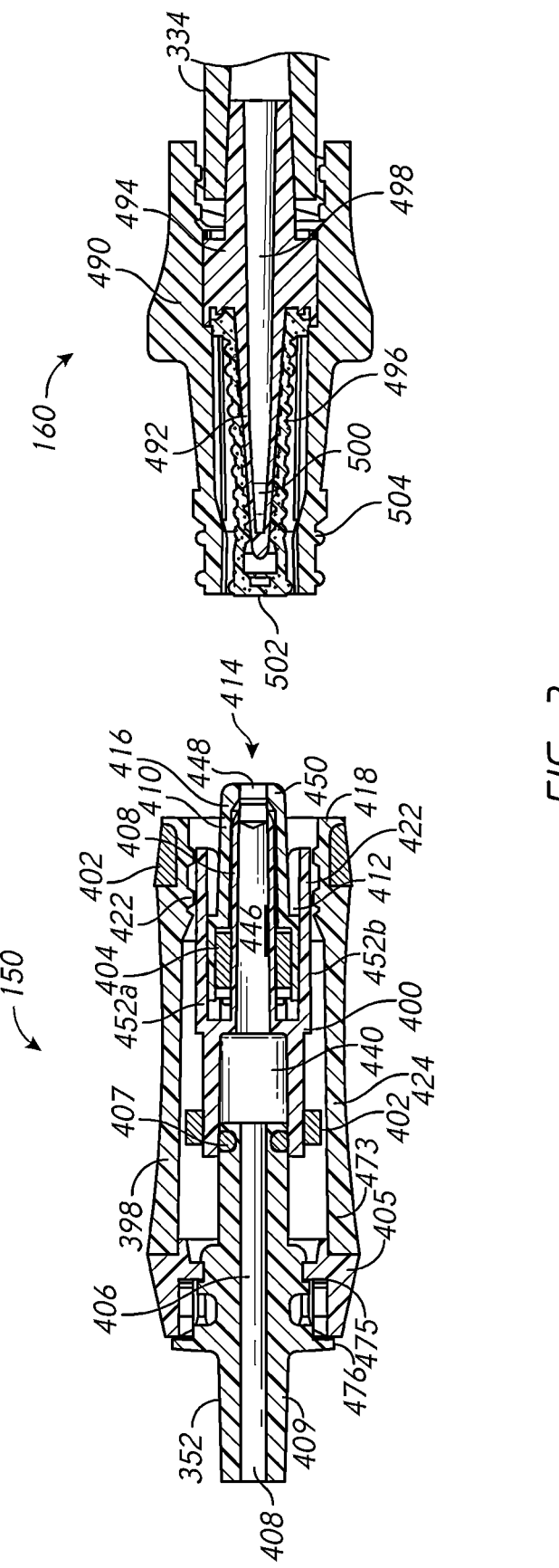
FIG. 3 is a cross-sectional view of two examples of male and female connectors among many types that can be used in one or more fluid delivery systems.

FIG. 3 illustrates some examples of closeable or resealable needleless male and female luer connectors 150, 160 that can be used with the inventions disclosed in this specification. Many other types of connectors can be used, including open-ended connectors and/or non-standard connectors, in appropriate circumstances. In some embodiments, as illustrated, the connectors are standard IV medical luer connectors, e.g., compliant with the ISO 594 standard. Any reference in this specification to a male connector should be understood to be interchangeable with a female connector, and any reference in this specification to a female connector should be understood to be interchangeable with a male connector, with appropriate adjustments. In some embodiments, fluid connector adaptors can be used to make appropriate connections between fluid lines. For example, in a situation where two male fluid connectors must be joined to complete a fluid pathway, an adaptor comprising a pair of female fluid connectors positioned in opposite directions on the fluid pathway and joined together with a fluid conduit or tubing can be attached to the male fluid connectors. In some embodiments, such an adaptor can be used, for example, to connect a cartridge 170 and an IV assembly 200 in which a male luer connector is positioned at the exit port of the cartridge 170 and a male luer connector is positioned on the end of the tubing 220 of the IV assembly 200.

A first connector 150 can be a closeable male luer connector that is configured to prevent fluid from escaping from or entering into the connector when it is not engaged with a corresponding female connector 160, but that allows fluid to flow when it is engaged with a corresponding female connector 160. In the embodiments shown, the first connector 150 is a version of the Spiros® closeable male connector manufactured by ICU Medical, Inc., of San Clemente, California. The first connector 150 can be configured to be attachable to a second connector 160, which is illustrated as a version of the Clave® closeable female connector, also manufactured by ICU Medical, Inc.

The first connector 150 can include a housing 398, a valve member 400, a resilient member 402, a sealing ring 404, an end cap 406, and an O-ring 407. The housing 398 can be generally tubular in shape, and can include a passageway 408 that extends axially through the housing. The housing 398 can include a male luer tip 410 that connects to the rest of the housing 398 at a base 412. The luer tip 410 can be generally tubular in shape, and the luer tip 410 can include a hole 414 at its end, providing access to the passageway 408. As illustrated, in some embodiments, connectors can be used to substantially entirely prevent fluid therein to leak, vaporize, or otherwise escape through apertures in the fluid pathway when the connectors are closed.

The luer tip 410 can be generally surrounded by a shroud 418 as illustrated. In some embodiments, the luer tip 410 extends a distance beyond the edge 420 of the shroud. The shroud 418 can include inner threads 422 on its interior surface. The inner threads 422 can be used for securing a female connector 160. The shroud can include an indented portion 424 that has a smaller outer diameter than the other portions of the housing. The indented portion 424 can be configured to engage a portion of the resilient member 402.

The housing 398 can be constructed from a variety of materials. The housing 398 can be constructed from a rigid material such as polycarbonate or other polymeric materials. In some embodiments, the housing 398 can be constructed from a hydrophobic material such as Bayer Makrolon, or any other suitable material. In some embodiments, the housing 398 can be formed from a substantially transparent material.

The connector 150 can include a fluid passageway 440 extending axially from an opening formed in a base portion 444 and into a tube 446. In some embodiments, the passageway 440 can be wider in the base portion 444 than in the tube 446. In some embodiments, the tube 446 includes a narrowed tip 448. In some embodiments, the tip 448 can have a tapered outer surface. In some embodiments, the tip 448 can be made from a flexible or compressible material, such as silicone rubber, to facilitate formation of the fluid seal between the tip 448 and the shelf 416. In some embodiments, the tube can include one or more holes 450 for providing access to the fluid passageway 440. The holes 450 can be formed, for example, in the tip 448 of the tube 446.

In some embodiments, the valve member 400 can include two struts 452a, 452b extending out from the base 444 and positioned on either side of tube 446, so that an open space is defined on either side of the tube. In some embodiments, the tube 446 can extend axially past the ends of the struts 452a, 452b. The valve member 400 can be constructed from a variety of materials, such as polycarbonate or other polymeric materials. In some embodiments, the valve member 400 can be constructed from the same material as the housing 398. In some embodiments, the valve member 400 and housing 398 can be constructed from different materials. In some embodiments, the valve member 400 can be constructed from multiple materials or from multiple pieces. For example, the tip 448 can be constructed from a material that is more flexible than the remainder of the valve member 400. In some embodiments, the valve member 400 can be formed from a substantially opaque material.

The resilient member 402 can include a first ring and a second ring connected to each other by longitudinally extending elastic members (not shown). The elastic members can be made from an elastic material that exerts a restoring force when stretched, such as silicone. Thus, if the rings are pulled apart, the elastic members function to restore the rings to their relaxed configuration. In some embodiments, the rings are also constructed from an elastic material, such as the same material used to form the elastic members. In some embodiments, the second ring can have a greater diameter than the first ring. In some embodiments, the second ring can have a tapered outer surface so that the end of the second ring that is closest to the first ring is wider than the end of the second ring that is furthest from the first ring.

The sealing ring 404 can be generally cylindrical in shape, and can have a bore extending axially therethrough. The sealing ring 404 can have a cylindrical body section and an O-ring located at one end of the body section 468. The sealing ring 404 can be constructed from a variety of materials. In some embodiments, the sealing ring 404 can be constructed from a deformable or elastic material such as a silicone rubber.

The end cap 406 can include a first end cap member 405 and a second end cap member 409. The second end cap member 409 can include an attachment portion, a plunger, and a disk portion located between the attachment portion and the plunger. The second end cap member 409 can have a fluid passageway axially positioned therein. In some embodiments, the plunger can be generally tubular in shape. In some embodiments, the outer surface of the plunger includes an indented region, which can be configured to receive the O-ring 407 therein.

The O-ring 407 can be constructed from an elastic material such as silicone rubber so that it can be stretched over the edge of the plunger and be seated in the indented region. In some embodiments, the O-ring can be constructed from the same material as the resilient member 402 and/or the sealing ring. In some embodiments, the O-ring can be sized so that when seated in the indented region, the thickest portion of the O-ring 407 extends radially outwardly a distance past the outer surface of the plunger.

The valve member 400 can be slidably inserted into the housing 398 so that the tube 446 enters the passageway 408. The narrowed tip 448 of the tube 446 can pass through the bore of the sealing ring 404 and into the male luer tip 410 until it abuts against the shelf 416. The tube 446 can have a width that substantially fills the bore 446 and presses against the O-ring 470 portion of the sealing ring 404 to form a fluid seal therebetween. The struts 452*a*, 452*b* can pass through holes in the housing 398, so that the struts 452*a*, 452*b* are positioned between the male luer tip 410 and the shroud 418.

The resilient member 402 can function to bias the valve member 400 against the housing 398. The first ring 460 can fit onto the lower portion 458 of the base 444 of the valve member 400, so that a surface of the ring 460 abuts against the protrusions 454. The second ring 462 can fit into the indented portion 424 of the housing. The elastic members can be positioned in channels.

The first connector 150 can be configured to engage a second connector 160. In some embodiments, the second connector 160 can be a closeable, resealable, needleless female connector, as illustrated. A variety of types of female connectors 332 can be used. The female connector 160 shown includes a housing 490, a spike 492, a base 494, and a resilient seal element 496. A fluid passageway 498 can pass through the base 494 and through the spike 492. The spike 492 can include one or more holes 500 providing fluid communication between the passageway 498 and the area outside the spike 492. The seal element 496 can be shaped and positioned to substantially surround the spike 492. The seal element 496 can include a closable aperture 502 or slit that can open to allow the tip of the spike 492 to pass through then end of the seal element 496 when the seal element 496 is compressed. The housing can include external threads 504 configured to engage the inner threads 422 on the housing 398 of the male connector 150. An end of the tubing 334 can be connected to the end of the female connector 160 by an adhesive, clamp, friction or pressure fitting, or other suitable manner to form a fluid tight connection.

In some embodiments, the housing 398, sealing ring 404, resilient member 402, valve member 400, and first end cap member 405 can rotate about the longitudinal axis with respect to the second end cap member 409. Thus, as the female connector 160 of the IV bag assembly is attached to the male connector 150, the female connector 160 can be held still while the housing 398 of the male connector 150 can rotate causing the threads 504, 422 to engage. Since the female connector 322 is not required to rotate during engagement and disengagement with the male connector 150, the tubing 334 can avoid being twisted or kinked and the user is not required to twist the IV bag to accommodate rotation of the female connector 322.

When not engaged with the female connector 160, the male connector 150 can be sealed. In some embodiments, fluid can enter the male connector 150 at the male connector 352 and pass through the passageway 478 of the end cap 406, through the passageway 440 of the valve member 400, through the holes 450, and into the portion of the passageway 408 of the male luer tip 410.

When the male connector 150 is engaged with the female connector 160, the external threads 504 of the female luer connector 332 can engage the inner threads 422 on the shroud 418, securing the female connector 160 to the male connector 150. The edge of the male luer tip 410 can press against and compress the resilient seal element 496 so that the spike 492 passes through the aperture 502 until the holes 500 are exposed. The end of the housing 490 of the female luer connector 332 can enter the space between the male luer tip 410 and the shroud 418 until it contacts the struts 452*a*, 452*b*. As the female luer connector 332 further engages the male connector 150, it can push on the struts 452*a*, 452*b* causing the entire valve member 400 to retract. As the valve member 400 retracts, the elastic members 464*a*, 464*b* of the resilient member 402 stretch. When the valve member 400 retracts, the tip 448 disengages from the shelf 416, breaking the fluid seal and allowing fluid pass from the passageway 408 in the housing 398 of the male connector 150 to the passageway 498 in the female connector 160 via the holes 500. When engaged, the resilient seal element 496 exerts a restoring force toward the male connector 150 that presses the end of the seal element 496 against the end of the male luer tip 410, forming a fluid seal therebetween. Thus, the fluid can be kept isolated from the external environment while it is transferred from the male connector 150 to the female connector 160.

The female connector 160 can be disengaged from the male connector 150. The restoring force exerted by the resilient seal element 496 of the female connector 160 can cause it to return to its closed position, sealing off its passageway 498. The elastic members of the resilient member 402 can exert a restoring force on the valve member 400, causing the valve member 400 to return to its closed position with its tip 448 abutted against the shelf 416 as the female connector 160 is disengaged. Any suitable connection can be provided at the fluid line connection points illustrated and/or described in this specification, including but not limited to those illustrated and/or described in connection with FIG. 3. Other connectors and/or other features of connectors can be used in addition to or instead of those illustrated and/or described in connection with FIG. 3.

Returning to FIGS. 1A and 1B, some methods of filling a custom IV assembly 200 with a particular amount or concentration of a therapeutic fluid or fluids for the needs of a particular patient or patients can comprise one or more or any combination of the following steps:

(i) obtaining, or instructing a user to obtain, a request from a healthcare practitioner or from a computer system for a custom-filled IV bag or a plurality of IV bags, each with a particular drug or drugs, and/or a particular dose or concentration of a drug or drugs, for a particular patient or patients;

(ii) obtaining, or instructing a user to obtain, an integral IV assembly 200 with one or more permanent, pre-attached bonds along an internal fluid path from an IV bag 210 through a resealable needleless connector 150, the IV assembly initially being empty of liquid or not completely filled with liquid;

(iii) attaching, or instructing a user to attach, one or more fluid inlets in the IV assembly 200 to one or more fluid dispensing outlets in the electronic fluid dispensing system 100, such as attaching a connector (e.g., a resealable, needleless male connector 150) of the IV assembly 200 to at least a first fluid channel of an electronic fluid dispensing system 100, such as by way of a complimentary connector 160 (e.g., a resealable, needleless female connector 160) in a disposable fluid cartridge 170 of the electronic fluid dispensing system 100, or by way of a suitable fluid connection adaptor, in the event that the connectors are not capable of forming a fluid connection (such as when a male-to-male connection or a female-to-female connection needs to be made);

(iv) providing, or instructing a user to provide, one or more user commands to the electronic fluid dispensing system to enable the transfer of a specific amount and/or concentration of a liquid or liquids from one or more fluid source containers 120 to the IV bag 210, such as by first passing fluid from at least one fluid source container 120 through a combination of one or more of an adaptor 165, one or more connectors 150, 160, a fluid cartridge 170, a liquid pump and/or mea-surer 140, and/or one or more connectors 150, 160, to the IV assembly 200, then permitting the fluid to continue progressing into the connector 150 of the IV assembly 200, into the long tubing 220 of the IV assembly 200, through the drip chamber 230 (if included) of the IV assembly 200, and into the IV bag 210, until the desired amount and/or concentration of the drug or drugs is received in the IV bag 210 (as illustrated, for example, in FIG. 1A), and/or providing one or more additional fluid filling lines in series or in parallel from the electronic fluid dispensing system 100 to the IV bag 210 (as illustrated, for example, in FIG. 1B), in either manner in some embodiments filling the IV bag 210 and pre-priming the drip chamber 230, long tubing 220, and fluid connector 150, as part of the same step and/or at generally the same time as filling the IV bag 210;

(v) detaching, or instructing a user to detach, the IV assembly 200 from the electronic fluid dispensing system 100, such as by detaching the connector 150 of the IV assembly 200 from the corresponding portion of the fluid channel of the electronic fluid dispensing system, and detaching any other fluid connections from any other fluid channels;

(vi) transporting, or instructing a user to transport, the custom-filled IV assembly 200 to a patient care site;

(vii) hanging or otherwise positioning, or instructing a user to hang or otherwise position, the IV bag 220 on an IV pole near a patient, such as by using a hanger 240 on the IV bag 220, or positioning the IV bag 220 on or in another type of holder; and/or (iix) extending, or instructing a user to extend, the pre-primed long tubing 220 from the hanging IV bag to an infusion pump (not shown), which is in turn configured to pump fluid to a patient, or extending, or instructing a user to extend, the pre-primed long tubing 220 from the IV bag directly to an infusion site near a patient, and attaching the pre-primed, connector 150 of the IV assembly 200 to a complimentary connector 160 on a fluid line that leads into the fluid pump or directly into the patient's vasculature.

As illustrated in FIG. 1B, in some embodiments in which the IV assembly includes multiple ports (also as shown in the example of FIG. 2), the step of filling the IV assembly 200 can include multiple fluid connections between the electronic fluid dispensing system 100 and the IV bag 210. Different types of fluids can be infused through different ports. In some embodiments, to save time, different types of fluids can be infused in parallel, as illustrated in FIG. 1B, generally simultaneously from the electronic fluid dispensing system 100 into the IV bag 210; however, in some embodiments, different fluids can be infused through different ports at different times.

All of the foregoing steps, or any combination of these steps, can be performed in some embodiments without requiring a healthcare practitioner to penetrate a spike-port on an IV bag with a hollow spike leading to a patient infusion line, and/or without requiring a healthcare practi-tioner to prime the fluid tubing, drip chamber (if used), and/or fluid connector (if used), of an IV assembly at or near the patient administration site and outside of a hazardous fume hood. As illustrated, in some embodiments, an IV bag can be provided without any spike-port at all or without any spike-port that has a septum configured to be pierced by a sharp spike. Rather, in some embodiments, the same fluid line in the IV assembly 200 can be used to fill the IV bag 210 with liquid in an upstream direction from the connector 150, through the long tubing 220 and drip chamber 230 (if used), to the IV bag 210, and then later to infuse the liquid from the IV bag 210 in a downstream direction through the same drip chamber 230 (if used), long tubing 220, and connector 150, to the patient injection site. The movement of liquid within the electronic fluid dispensing system 100 and/or the filling of the IV assembly 200 can be accomplished with any pump, such as a syringe pump or a peristaltic pump. In some embodiments, a syringe pump or a peristaltic pump is not used.

In some embodiments, during the IV assembly filling stage, after a desired quantity of therapeutic agent is deliv-ered to the IV assembly 200, an additional volume of liquid, such as an inert or benign liquid, can be pushed through or made to "chase" the drug through the lower fluid pathway of the IV assembly 200, such as through the bottom connector 150, the tubing 520, the drip chamber 530 (if used), and/or into the IV bag 210, so as to flush or move any potentially harmful liquid or vapors an effective distance into the IV assembly 200 and away from persons who are transporting, storing, and/or administering the therapeutic liquid to a patient.

Figure 4:
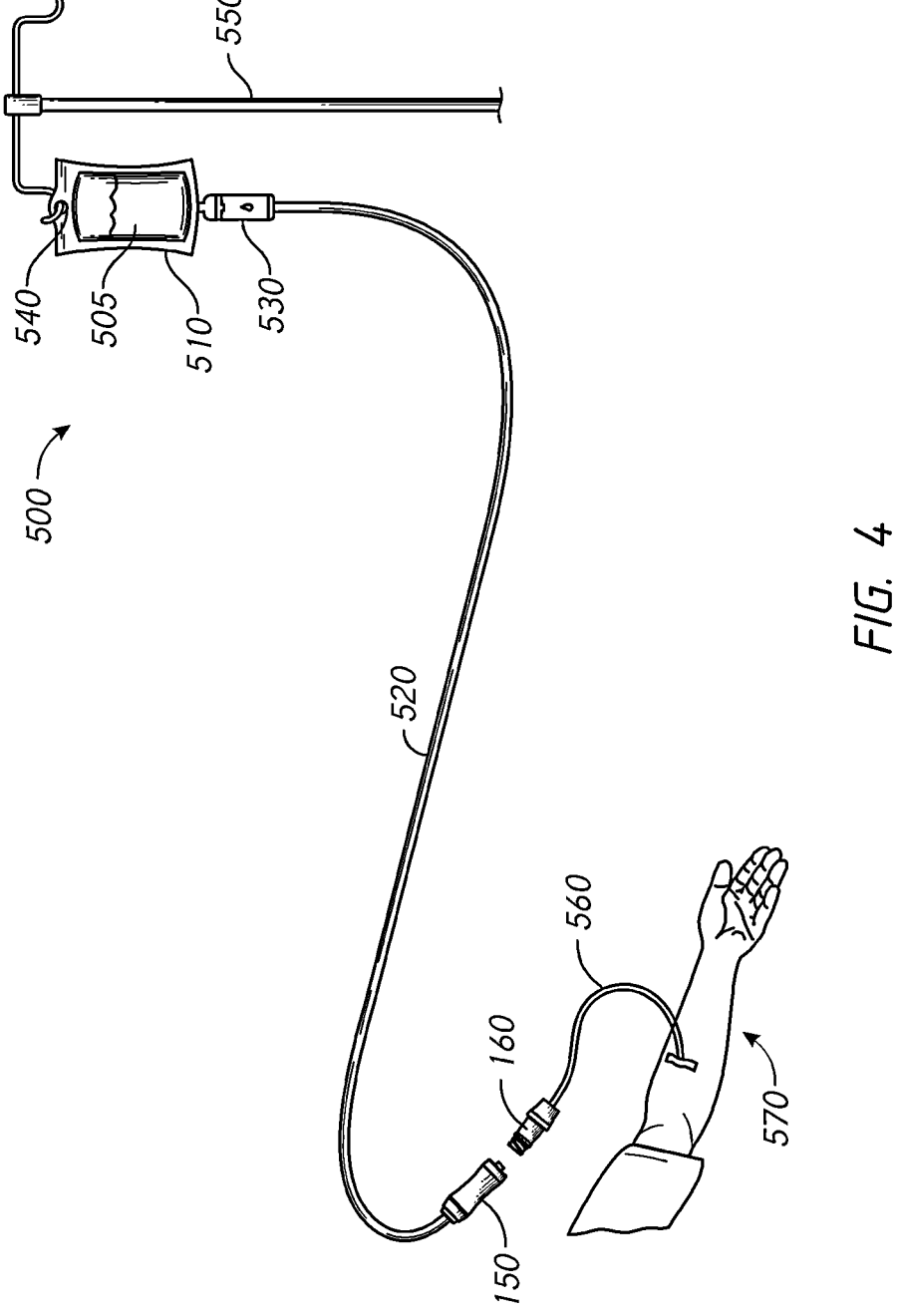
FIG. 4 shows a pre-filled, pre-primed IV assembly with an integral liquid delivery path in liquid communication with a patient.

FIG. 4 illustrates an example of a pre-primed IV assembly 500 at a patient care site that has been filled using some type of an electronic fluid dispensing system, such as the elec-tronic fluid dispensing system of FIGS. 1A and 1B. The IV bag 510 of the IV assembly 500 is hung with a hanger 540 on an IV pole 550. The liquid 505 containing one or more therapeutic agents, such as antibiotics, pain management medication, chemotherapy, and/or immunosuppressive drugs, in the IV bag 510 moves under the influence of gravity from an exit location at the bottom of the IV bag 510, into the drip chamber 530 (if used), into the long tube 520, through the connectors 150,160, through the patient catheter 560, and into the patient 570. In some embodiments, the one or more therapeutic agents in the IV bag 510 move from the IV bag 510, into the drip chamber (530) if used, into the long tube 520, through the end connector on the IV assembly 500 if used, and into an input connector 160 (not shown) on an IV pump assembly (not shown). In the illustrated embodiment, the distance or length of the pre-primed fluid path of the IV assembly 500, from the exit location on the IV bag 510 to the resealable connector 160 on the patient catheter 560, is at least about 2½ feet and/or less than or equal to about 3½ feet, which is sufficiently long to provide a comfortable attachment distance between the IV bag 510 and the patient when the patient is in a generally flat position on a hospital bed or when the patient is sitting in a chair with a generally horizontally extended arm. Many other types, configurations, and lengths of tubing can be used.

The following is claimed:

1. A method of enabling pre-filling of custom IV bags, the method comprising:
    providing an electronic fluid transfer system configured to receive instructions from a user regarding an amount of fluid to be transferred from one or more source containers into an IV bag;
    providing a pre-assembled IV assembly comprising an IV bag, providing a tubing permanently bonded in fluid communication with the IV bag, the tubing-bonding occurring before the pre-assembled IV assembly is provided to a user, such that the user is not required to attach the tubing to the IV assembly, and providing a connector permanently bonded to the tubing, the connector-bonding occurring before the pre-assembled IV assembly is provided to a user, such that the user is not required to attach the closeable connector to the tubing, the connector comprising an open position and a closed position for providing a selectively accessible closed fluid system, and the tubing having a length of at least about 2½ feet so as to be configured to be extendable from a hanging position on a pole stand to a connector attached to a patient or to an infusion pump and further configured to provide fluid communication to the IV bag for both filling of the IV bag and delivery of the fluid from the IV bag to the patient;
    instructing a user to connect the connector of the IV assembly to the electronic fluid transfer system, placing the IV assembly in fluid communication with the electronic fluid transfer system;
    instructing a user to transfer fluid from one or more source containers in the electronic fluid transfer system to the IV bag, such that the fluid is transferred by the electronic fluid transfer system through the connector, then through the tubing, then into the IV bag, to produce a pre-primed IV assembly with fluid extending from the connector through the tubing and into the IV bag.

2. The method of claim 1, wherein the pre-assembled IV assembly comprises a drip chamber positioned between the tubing and the IV bag.

3. The method of claim 1, wherein the connector is a closeable connector.

4. The method of claim 1, wherein the connector is a resealable connector.

5. The method of claim 4, wherein the connector is a needleless connector.

6. The method of claim 1, wherein the connector is a male connector.

7. The method of claim 5, wherein the connector is a female connector.

8. The method of claim 6, wherein the male connector is configured to prevent conveyed or residual fluid from leaking out after disconnection.

9. The method of claim 1, wherein the electronic fluid transfer system comprises a drive motor.

10. The method of claim 9, wherein the electronic fluid transfer system comprises a driving mechanism.

11. The method of claim 10, wherein the electronic fluid transfer system comprises a microprocessor.

12. The method of claim 11, wherein the electronic fluid transfer system comprises a memory.

13. The method of claim 12, wherein the electronic fluid transfer system comprises communications hardware and software to enable electronic communication with a network.

14. The method of claim 12, wherein the electronic fluid transfer system comprises an electronic display.

15. The method of claim 12, wherein the electronic fluid transfer system comprises a user input system.

* * * * *